(12) United States Patent
Ylera

(10) Patent No.: US 12,188,023 B2
(45) Date of Patent: Jan. 7, 2025

(54) DISPLAY SYSTEMS FOR PROTEINS OF INTEREST

(71) Applicant: BIO-RAD ABD SEROTEC GMBH, Puchheim (DE)

(72) Inventor: Francisco Ylera, Munich (DE)

(73) Assignee: BIO-RAD ABD SEROTEC GMBH, Puchheim (DE)

( * ) Notice: Subject to any disclaimer, the term of this patent is extended or adjusted under 35 U.S.C. 154(b) by 53 days.

(21) Appl. No.: 17/935,139

(22) Filed: Sep. 26, 2022

(65) Prior Publication Data

US 2023/0193297 A1 Jun. 22, 2023

Related U.S. Application Data

(62) Division of application No. 16/375,894, filed on Apr. 5, 2019, now Pat. No. 11,453,883.

(60) Provisional application No. 62/652,938, filed on Apr. 5, 2018.

(51) Int. Cl.
| | |
|---|---|
| *C12N 15/70* | (2006.01) |
| *C07K 16/24* | (2006.01) |
| *C07K 16/32* | (2006.01) |
| *C07K 19/00* | (2006.01) |
| *C12N 7/00* | (2006.01) |
| *C12N 15/10* | (2006.01) |
| *C12N 15/85* | (2006.01) |

(52) U.S. Cl.
CPC .......... *C12N 15/70* (2013.01); *C07K 16/241* (2013.01); *C07K 16/32* (2013.01); *C07K 19/00* (2013.01); *C12N 7/00* (2013.01); *C12N 15/1037* (2013.01); *C12N 15/85* (2013.01); *C07K 2317/21* (2013.01); *C07K 2317/24* (2013.01); *C07K 2317/55* (2013.01); *C12N 2795/00051* (2013.01)

(58) Field of Classification Search
CPC ..................................................... C12N 15/70
See application file for complete search history.

(56) References Cited

U.S. PATENT DOCUMENTS

| | | | |
|---|---|---|---|
| 5,264,365 A | 11/1993 | Georgiou et al. | |
| 5,616,686 A | 4/1997 | Fischetti et al. | |
| 6,753,136 B2 | 6/2004 | Lohning | |
| 6,828,121 B2 | 12/2004 | Chen | |
| 7,785,859 B2 | 8/2010 | Lohning | |
| 7,811,973 B2 | 10/2010 | Burioni et al. | |
| 8,216,822 B2 | 7/2012 | Mehta et al. | |
| 8,735,330 B2 | 5/2014 | Løset | |
| 8,969,038 B2 | 3/2015 | Ellis et al. | |
| 8,969,039 B2 | 3/2015 | Ellis et al. | |
| 9,062,097 B2 | 6/2015 | Prassler et al. | |
| 9,109,216 B2 | 8/2015 | Ellis et al. | |
| 9,133,500 B2 | 9/2015 | Frisch et al. | |
| 9,481,715 B2 | 11/2016 | Vernet et al. | |
| 9,547,003 B2 | 1/2017 | Howarth | |
| 9,688,775 B2 | 6/2017 | Simmons et al. | |
| 9,725,516 B2 | 8/2017 | Walper et al. | |
| 9,951,365 B2 | 4/2018 | Bassett et al. | |
| 9,994,622 B2 | 6/2018 | Blais et al. | |
| 10,526,379 B2 | 1/2020 | Howarth | |
| 10,745,730 B2 | 8/2020 | Gottesman | |
| 11,059,867 B2* | 7/2021 | Howarth .............. | C07K 14/315 |
| 11,453,883 B2 | 9/2022 | Ylera | |
| 11,674,164 B2 | 6/2023 | Hentrich et al. | |
| 2003/0198956 A1 | 10/2003 | Makowski et al. | |
| 2012/0259101 A1 | 10/2012 | Tan et al. | |
| 2013/0029377 A1 | 1/2013 | Caparon et al. | |
| 2014/0323691 A1 | 10/2014 | Tan et al. | |
| 2016/0222372 A1* | 8/2016 | Walper ..................... | C12N 9/96 |
| 2016/0305947 A1 | 10/2016 | Pierce et al. | |
| 2017/0146522 A1 | 5/2017 | Howarth | |

(Continued)

FOREIGN PATENT DOCUMENTS

| | | |
|---|---|---|
| CN | 101258243 | 9/2008 |
| CN | 101802195 | 8/2010 |

(Continued)

OTHER PUBLICATIONS

Albrecht, Hugette et al. "Production of Soluble ScFvs with C-Terminal-Free Thiol for Site-Specific Conjugation or Stable Dimeric ScFvs on Demand," Bioconjugate Chem. Dec. 31, 2003, vol. 15, No. 1, pp. 16-26.

Fierer, Jacob O. et al. "SpyLigase peptide-peptide ligation polymerizes affibodies to enhance magnetic cancer cell capture," PNAS, 2014, pp. 1-6.

Mazor, Yariv et al. "Selection of full-length IgGs by tandem display on filamentous phage particles and *Escherichia coli* fluorescence-activated cell sorting screening," the FEBS Journal, Journal No. 227, 2010, pp. 2291-2303.

Nguyen et al. "Butelase 1 is an Asx-specific ligase enabling peptide macrocyclization and synthesis," nature chemical biology, vol. 10, Jul. 20, 2014, pp. 732-738.

Qi, Huan et al. "Phagemid Vectors for Phage Display: Properties, Characteristics and Construction," Journal of Molecular Biology, Jan. 30, 2012, vol. 417, pp. 129-143.

(Continued)

*Primary Examiner* — Albert M Navarro
(74) *Attorney, Agent, or Firm* — SALIWANCHIK, LLOYD & EISENSCHENK

(57) ABSTRACT

Described herein is a protein display selection method which uncouples a protein of interest (POI) library from the display selection system. Display of the POI can be achieved by forming a covalent bond between the POI and the anchor protein post expression either by enzymatic protein ligation (e.g. SpyLigase, SnoopLigase, sortase, butelase, peptiligase etc.) or by spontaneous covalent bond formation (e.g. Spy-Tag/SpyCatcher, SnoopTag/SnoopCatcher, etc.). The POI library is fused to a tethering sequence, for example SpyTag, at the C-terminus of the POI which then forms a covalent bond to a capture sequence found on an anchor protein, for example, the SpyCatcher-fused anchor protein, e.g., a SpyCatcher-geneIII protein (SpyCatcher-pIII) fusion, for the most common form of phage display. Nucleic acid constructs, host cell systems and methods of producing the protein display systems are also provided.

16 Claims, 6 Drawing Sheets

Specification includes a Sequence Listing.

(56) References Cited

U.S. PATENT DOCUMENTS

| | | |
|---|---|---|
| 2018/0052081 A1 | 2/2018 | Kohman |
| 2018/0327446 A1 | 11/2018 | Fong et al. |
| 2018/0344871 A1 | 12/2018 | Tsourkas et al. |
| 2019/0178878 A1 | 6/2019 | Howarth |
| 2020/0299358 A1 | 9/2020 | Knappik et al. |
| 2020/0299369 A1 | 9/2020 | Knappik |
| 2020/0299746 A1 | 9/2020 | Hentrich et al. |
| 2022/0135628 A1 | 5/2022 | Howarth et al. |

FOREIGN PATENT DOCUMENTS

| | | |
|---|---|---|
| CN | 103074359 | 5/2013 |
| CN | 108697733 | 1/2017 |
| CN | 106967658 | 9/2020 |
| EP | 0 393 045 | 10/1990 |
| EP | 1 341 899 | 9/2003 |
| EP | 1144607 | 12/2008 |
| EP | 2190987 | 11/2012 |
| EP | 2534484 | 11/2014 |
| EP | 2 993 231 | 3/2016 |
| KR | 102235549 | 4/2021 |
| WO | WO 2011/098772 | 8/2011 |
| WO | WO 2013/045632 | 4/2013 |
| WO | WO 2013/171156 | 11/2013 |
| WO | WO 2016/154621 | 9/2016 |
| WO | WO 2016/183387 | 11/2016 |
| WO | WO 2016/193746 | 12/2016 |
| WO | WO 2017/058114 | 4/2017 |
| WO | WO 2017/070742 | 5/2017 |
| WO | WO 2017/112784 | 6/2017 |
| WO | WO 2018/053180 | 3/2018 |
| WO | WO 2018/189517 | 10/2018 |
| WO | WO 2018/197854 | 11/2018 |
| WO | WO 2018/220386 | 12/2018 |
| WO | WO 2019/006046 | 1/2019 |

OTHER PUBLICATIONS

Reddignton, Samuel et al. Secrets of a covalent interaction for biomaterials and biotechnology: SpyTag and SpyCatcher, Current Opinion in Chemical Biology, Oct. 20, 2015, vol. 29, pp. 94-99.

Rondot, Susanne et al. "A helper phage to improve single-chain antibody presentation in phage display," Nature Biotechnology, Jan. 2001, vol. 19, pp. 75-78.

Rothe, Christine et al. "The Human Combinatorial Antibody Library HuCAL Gold Combines Diversification of All Six CDRs According to the Natural Immune System with a Novel Display Method for Efficient Selection of High-Affinity Antibodies," J. Mol. Bio., 2008, vol. 376, pp. 1182-1200. (Available online: Dec. 15, 2017).

Thiel, Ilka V. et al. "An Atypical Naturally Split Intein Engineered for Highly Efficient Protein Labeling," Angew. Chem. Int. Ed., 2014, vol. 53, 1306-1310.

Toplak, Ana et al. "Peptiligase, an Enzyme for Efficient Chemoenzymatic Peptide Synthesis and Cyclization in Water," Adv. Synth. Catal. May 24, 2016, vol. 358, pp. 2140-2147.

Veggiani, Gianluca et al. "Programmable polyproteams built using twin peptide superglues," PNAS, Feb. 2, 2016, vol. 113, No. 5, pp. 1202-1207.

Wang, Kevin Caili et al. "Adapter-Directed Display: A Modular Design for Shutting Display on Phage Surfaces," J. Mol. Biol. , Dec. 4, 2009, vol. 395, 1088-1101.

Ward, R.L. et al. "Retrieval of human antibodies from phage-display libraries using enzymatic cleavage," Journal of Immunological Methods, 1996, vol. 189, pp. 73-82.

Yumura, Kyohei et al. "Use of SpyTag/SpyCatcher to construct bispecific antibodies that target two epitopes of a single antigen," Oxford University Press on behalf of Japanese Biochemical Society, 2017, pp. 1-27.

Zakeri, Bijan et al. Peptide tag forming a rapid covalent bond to a protein, through engineering a bacterial adhesin, PNAS, vol. 109, No. 12, Mar. 20, 2012, pp. 4347-4348.

Schmohl, Lena et al. "Sortase-mediated ligations for the site-specific modification of proteins," Current Opinion in Chemical Biology, Oct. 6, 2014, vol. 22, pp. 122-128.

Siegmund, Vanessa et al. "Spontaneous Isopeptide Bond Formation as a Powerful Tool for Engineering Site-Specific Antibody-Drug Conjugates," Scientific Reports, Dec. 16, 2016, 6:39291, DOI: 10.103/srep39291, pp. 1-9.

Van Den Berg van Saparoea, H. B. et al. "Display of Recombinant Proteins on Bacterial Outer Membrane Vesicles by Using Protein Ligation" Applied and Environmental Microbiology, Feb. 9, 2018, pp. 1-17, vol. 84, Issue 8, e02567-17.

Schmohl, L. et al. "Engineering sortase A by screening a second-generation library using phage display" Journal of Peptide Science, Feb. 10, 2017, pp. 631-635, Supporting Information pp. 1-14, vol. 23, Nos. 7-8.

Nguyen, H. D. et al. "Analysis and application of Bacillus subtilis sortases to anchor recombinant proteins on the cell wall" AMB Express, Jul. 21, 2011, pp. 1-11, vol. 1, No. 22.

Borodina, I. et al. "Disply of wasp venom allergens on the cell surface of Saccharomyces cerevisiae" Microbial Cell Factories, Sep. 24, 2010, pp. 1-13, vol. 9, No. 74.

Hatlem, D. et al. "Catching a SPY: Using the SpyCatcher-SpyTag and Related Systems for Labeling and Localizing Bacterial Proteins" International Journal of Molecular Sciences, Apr. 30, 2019, pp. 1-19, vol. 20, No. 9.

International Search Report and Written Opinion in International Application No. PCT/IB2019/000339, Sep. 13, 2019, pp. 1-22.

Alam, M. K. et al. "Site-Specific Fluorescent Labeling of Antibodies and Diabodies Using SpyTag/SpyCatcher System for In Vivo Optical Imaging" Mol Imaging Biol., 2018, pp. 54-66, vol. 21.

Alam, M. K. et al. "Synthetic Modular Antibody Construction Using the SpyTag/SpyCatcher Protein Ligase System" ChemBioChem, 2017, pp. 2217-2221, vol. 18, No. 22.

International Search Report and Written Opinion in International Application No. PCT/IB2020/000197, Aug. 28, 2020, pp. 1-18.

Keeble, A. H. et al. "Evolving Accelerated Amidation by SpyTag/SpyCatcher to Analyze Membrane Dynamics" Ange. Chem. Int. Ed., 2017, pp. 16521-16525, vol. 56.

International Search Report and Written Opinion in International Application No. PCT/IB2020/000134, Aug. 27, 2020, pp. 1-18.

Meerman, H. et al. "Construction and Characterization of a Set of E. coli Strains Deficient in All Known Loci Affecting the Proteolytic Stability of Secreted Recombinant Proteins," Biotechnology, Nov. 23, 1994, pp. 1107-1110, vol. 12.

Chen, C. et al. "High-Level Accumulation of a Recombinant Antibody Fragment in the Periplasm of Escherichia coli Requires a Triple-Mutant (degP prc spr) Host Strain" Biotechnology and Bioengineering, published online Jan. 26, 2004, pp. 463-474, vol. 85, No. 5.

Ellis, M. et al. "Development of a High Yielding E. coli Periplasmic Expression System for the Production of Humanized Fab' Fragments" Biotechnol. Prog., 2017, pp. 212-220, vol. 33, No. 1.

Alves, N. J. et al. "Bacterial Nanobioreactors-Directing Enzyme Packaging into Bacterial Outer Membrane Vesicles" ACS Appl. Mater Interfaces, 2015, pp. 24963-24972, vol. 7.

International Search Report and Written Opinion in International Application No. PCT/IB2020/000172, Jul. 27, 2020, pp. 1-18.

Zakeri, B. et al. "Peptide tag forming a rapid covalent bond to a protein, through engineering a bacterial adhesin" PNAS, published online Feb. 24, 2012, pp. E680-E697 and supporting pp. 1-19, vol. 109, No. 12.

Liu, Z. et al. "A novel method for synthetic vaccine construction based on protein assembly" Scientific Reports, 2014, pp. 1-8, vol. 4, No. 7266.

Brune, K. D. et al. "Plug-and-Display: decoration of Virus-Like Particles via isopeptide bonds for modular immunization" Scientific Reports, 2016, pp. 1-13, vol. 6, No. 19234.

Abe, H. et al. "Split Spy0128 as a Potent Scaffold for Protein Cross-Linking and Immobilization" Bioconjugate Chem., 2013, vol. 24, No. 2, pp. 242-250.

Akiba, H. et al. "Generation of biparatopic antibody through two-step targeting of fragment antibodies on antigen using SpyTag and SpyCatcher" Bioechnology Reports, 2020, pp. 1-7, vol. 25, e00418.

(56) References Cited

OTHER PUBLICATIONS

Alam, M. et al. "A novel synthetic trivalent single chain variable fragment (tri-scFv) construction platform based on the SpyTag/SpyCatcher protein ligase system." BMC Biotechnology, 2018, vol. 18, No. 55, pp. 1-8.
Albrecht, H. et al. "Monospecific bivalent scFv-SH: Effects of linker length and location of an engineered cysteine on production, antigen binding activity and free SH accessibility" *Journal of Immunological Methods*, available online Feb. 3, 2006, pp. 100-116, vol. 310.
Batonick, M. et al. "pMINERVA: A donor-Acceptor System for the in vivo Recombineering of scFv into IgG molecules." J Immunol Methods, 2016 vol. 431, pp. 22-30.
Berman, H.M. et al. "The Protein Data Bank." Nucleic Acids Res. 2000, vol. 28, No. 1, pp. 235-242.
Brannon, J.R. "Inhibition of Outer Membrane Proteases of the Omptin Family by Aprotinin," Infect Immun., 2015, vol. 83, pp. 2300-2311.
Caspi, J. et al. "Distribution of split DnaE inteins in cyanobacteria," Mol Microbiol, 2003, vol. 50, No. 5, pp. 1569-1577.
Chen, W. and Georgiou, G., 2002, "Cell-surface display of heterologous proteins: From high-throughput screening to environmental applications," Biotechnol Bioeng. 79:496-503.
Chen, X. et al. "Fusion protein linkers: Property, design and functionality" *Advanced Drug Delivery Reviews*, available online Sep. 29, 2012, pp. 1357-1369, vol. 65.
Chichili et al. "Linkers in the structural biology of protein-protein interactions," Protein Sci., Sep. 7, 2012, vol. 22:153-167.
Cho, M.S. Establishment of a Human Somatic Hybrid Cell Line for Recombinant Protein Production. J Biomed Sci., 2002, vol. 9, pp. 631-638.
Choi, J. et al. "Protein Trans-splicing and Characterization of a Split Family B-type DNA Polymerase from the Hyperthermophilic Archaeal Parasite Nanoarchaeum equitans," J Mol. Biol., 2006, vol. 356, pp. 1093-1106.
Cloutier, S. et al. "Streptabody, a high avidity molecule made by tetramerization of in vivo biotinylated, phage display-selected scFv fragments on streptavidin," Molecular Immunology, 2000, vol. 37, pp. 1067-1077.
Cuesta Angel, M. et al. "Multivalent antibodies: when design surpasses evolution." Trends Biotechnol, 2010, vol. 28, pp. 355-362.
Dassa, B. et al. "Trans Protein Splicing of Cyanobacterial Split Inteins in Endogenous and Exogenous Combinations. Biochemistry," 2007, vol. 46, pp. 322-330.
Datsenko, K.A. et al. "One-step inactivation of chromosomal genes in *Escherichia coli* K-12 using PCR products," Proc Natl Acad Sci USA, 2000, vol. 97, No. 12, pp. 6640-6645.
Dictionary "Unique" accessed from dictionary.com on Mar. 20, 2023 (Year: 2023), p. 1.
Ducancel, F. et al. "Recombinant Colorimetric Antibodies: Construction and characterization of a Bifunctional F(ab)2/Alkaline Phosphatase Conjugate Produced in *Escherichia coli*," Bio/Technol, 1993, vol. 11, pp. 601-605.
Ezkurdia, I. et al. "Protein Structural Domains: Definition and Prediction," Curr Protoc Protein Sci., Supplement 66, Nov. 2011, Chapter 2, doi: 10.1002/0471140864.ps0214s66, pp. 2.14.1-2.14.16.
Geller, B. L. "Antibacterial antisense," Curr. Opin. Mol. Ther., 2005, vol. 7, pp. 109-113.
Gingrich, J.C. et al. "Multiplex Detection and Quantitation of Proteins on Western Blots Using Fluorescent Probes," Biotechniques, Sep. 2000, vol. 29, No. 3, pp. 636-642.
Hentrich, C. et al. "Periplasmic expression of SpyTagged antibody fragments enables rapid modular antibody assembly" *Cell Chemical Biolog*, May 20, 2021, pp. 1-30, vol. 28.
IMGT definitions according to Lefranc M.-P., De R.K., Tomar N. Immunoinformatics of the V, C and G domains: IMGT® definitive system for IG, TR and IgSF, MH and MhSF, Immunoinformatics: From Biology to Informatics, 2014, vol. 1184 2nd edition Springer, NY Humana Press (p. 59-107).
Jia, L. et al. "Polymeric SpyCatcher scaffold enables bioconjugation in a ratio-controllable manner," Biotechnology Journal, Mar. 16, 2017, vol. 12, No. 12, oi:[10.1002/biot.201700195].
Keeble, A. H., Howarth, M., 2019, Insider information on successful covalent protein coupling with help from SpyBank. Methods in Enzymology. 617: 443-461, doi.org/10.1016/bs.mie.2018.12.010.
Keeble, A.H. et al. "Approaching infinite affinity through engineering of peptide-protein interaction," Proc. Natl. Acad. Sci., 2019, vol. 116, pp. 26526-26533.
Keiler, K. et al. "Identification of Active Site Residues of the Tsp Protease," J. Biol. Chem., 1995, vol. 270, No. 48, pp. 28864-28868.
Knappik, A. et al. "Recombinant antibody Expression and Purification," In: Walker, J.M. editor. The Protein Protocols Handbook. 3rd edition. New York: Humana Press Inc., 2009, pp. 1929-1943.
Knappik, A. et al. "Development of Recombinant Human IgA for Anticardiolipin Antibodies Assay Standardization," Annals of the New York Academy of Sciences, 2009, vol. 1173, pp. 190-198.
Ko, S. et al. "Engineering antibodies for dual specificity and enhanced potency" *Biotechnol Bioproc E*, 2015, pp. 201-210, vol. 20. https://doi.org/10.1007/s12257-014-0575-6 (Year: 2015).
Li et al. "Structural Analysis and Optimization of the Covalent Association between SpyCatcher and a Peptide Tag," J. Mol. Biol., 2014, vol. 426, No. 2, pp. 309-317.
Liu, X.-Q. et al. "Split dnaE Genes Encoding Multiple Novel Inteins in Trichodesmium erythraeum," J. Biol. Chem., 2003, vol. 278, pp. 26315-26318.
Mauro, V.P. "Codon Optimization in the Production of Recombinant Biotherapeutics: Potential Risks and Considerations." BioDrugs: clinical immunotherapeutics, biopharmaceuticals and gene therapy, Feb. 1, 2018, vol. 32, No. 1, pp. 69-81.
Nguyen et al. "Butelase-mediated cyclization and ligation of peptides and proteins," Nature protocols, 2016, vol. 11, No. 10, pp. 1977-1988.
Pack, P. et al. "Miniantibodies: use of Amphipathic Helices to Produce Functional, Flexibly Linked Dimeric Fv Fragments with High Avidity in *Escherichia coli*," Biochemistry, 1992, vol. 31, No. 6, pp. 1579-1584.
Pack, P. et al. "Tetravalent Miniantibodies with High Avidity Assembling in *Escherichia coli*." Journal of Molecular Biology, 1995, vol. 246, pp. 28-34.
Pallen, M. et al. "The HtrA family of serine proteases" Mol Microbiol, 1997, 26:209-21.
Pluckthun, A. "Antibodies from *Escherichia coli*," Nature, Oct. 4, 1990, vol. 347, No. 6292, pp. 497-498.
Prassler, J. et al. "HuCAL Platinum, a synthetic Fab Library Optimized for Sequence Diversity and Superior Performance in Mammalian Expression Systems," J. Mol. Biol., 2011, vol. 413, No. 1, pp. 261-278.
Prouty, W.F. et al. "Effects of Protease Inhibitors on Protein Breakdown in *Escherichia coli*." J. Biol. Chem., 1972, vol. 247, pp. 3341-3352.
Qi, F. et al. "Evolutionary analysis of polyproline motifs in *Escherichia coli* reveals their regulatory role in translation," PLOS Computational Biology, Feb. 1, 2018, vol. 14, No. 2, e1005987.
Rheinnecker, M. et al. "Multivalent Antibody Fragments with High Functional Affinity for a Tumor-Associated Carbohydrate Antigen." J Immunol, 1996, vol. 157, pp. 2989-2997.
Shah, N. et al. "Split Inteins: Nature's Protein Ligases," Israel Journal of Chemistry, 2011, vol. 5, (8-9), pp. 854-861.
Silber, K. et al. "Tsp: a tail-specific protease that selectively degrades proteins with nonpolar C termini," PNAS, 1991, vol. 89, pp. 295-299.
Skerra and Pluckthun, "Assembly of a Functional Immunoglobulin Fv Fragment in *Escherichia coli*". Science, 1988, vol. 240, 4855, pp. 1038-1041.
Sutherland, A. R. et al. "Post-translational Assembly of Protein Parts into Complex Devices by Using SpyTag/SpyCatcher Protein Ligase" Chem BioChem, 2019, pp. 319-328, vol. 20.

(56) References Cited

OTHER PUBLICATIONS

Tan et al. "Kinetic Controlled Tag-Catcher Interactions for Directed Covalent Protein Assembly," PLOS ONE, 2016, vol. 11, No. 10, e0165074.

Waugh, D.S. "Crystal structures of MBP fusion proteins," Protein Sci., Dec. 19, 2015, vol. 25, pp. 559-571.

Wu, C. et al. "Twin disulfides for orthogonal disulfide pairing and the directed folding of multicyclic peptides," Nat Chem., 2012, vol. 4, pp. 1044-1049.

Wu, H. et al. "Protein trans-splicing by a split intein encoded in a split DnaE gene of *Synechocystis* sp. PCC6803," Proc Natl Acad Sci., 1998, vol. 95, pp. 9226-9231.

Zettler, J. et al. "The Naturally Split Npu DnaE intein exhibits an extraordinarily high rate in the protein trans-splicing reaction," FEBS Letters, 2009, 553:909-914.

Bhatta, P. et al. "Bispecific antibody target pair discovery by high-throughputphenotypic screening using in vitro combinatorial Fab libraries" *MAbs*, 2021, pp. 1-20, vol. 13, No. 1, 1859049.

Deng, J.-R. et al. "Chemoselective and photocleavable cysteinemodification of peptides and proteins using isoxazoliniums" *Commun Chem*, 2019, pp. 1-10, vol. 2, No. 93.

Dovala, D. et al. "Rapid analysis of protein expression and solubility with the SpyTag-SpyCatcher system" *Protein Expr Purif*, 2016, pp. 44-51, vol. 117.

Hartzell, E.J. et al. "Engineering a Blue Light Inducible SpyTag System (BLISS)" *J Am Chem Soc*, 2021, pp. 8572-8577, vol. 143, No. 23.

Hentrich, C., et al. "Engineered Reversible Inhibition of SpyCatcher Reactivity Enables Rapid Generation of Bispecific Antibodies" *bioRxiv*, Oct. 2023, pp. 1-32, https://doi.org/10.1101/2023.10.27.564397.

Hofmann, T. et al. "Intein mediated high throughput screening for bispecific antibodies" *MAbs*, 2020, pp. 1-16, vol. 12, No. 1, e1731938.

Kantner, T. et al. "In Situ Quenching of Trialkylphosphine Reducing Agents Using Water-Soluble PEG-Azides Improves Maleimide Conjugation to Proteins" *ACS Omega*, 2017, pp. 5785-5791, vol. 2, No. 9.

Ma, J. et al. "Bispecific Antibodies: From Research to Clinical Application" *Frontiers in Immunology*, 2021, pp. 1-19, vol. 12, Article 626616.

Mahmoodi, M. M. et al. "6-Bromo-7-hydroxy-3-methylcoumarin (mBhc) is an efficient multi-photon labile protecting group for thiol caging and three dimensional chemical patterning" *Org Biomol Chem*, Sep. 21, 2016, pp. 1-29, vol. 14, No. 35.

Mei, L. et al. "Rapid Production of Bispecific Antibodies from Off-the-Shelf IgGs with High Yield and Purity" *Bioconjugate Chemistry*, 2022, pp. 1-19, vol. 33, No. 1.

Min, D. et al. "A simple DNA handle attachment method for single molecule mechanical manipulation experiments" *Protein Sci*, 2016, pp. 1535-1544, vol. 25, No. 8.

Pessino, V. et al. "Covalent Protein Labeling by SpyTag-SpyCatcher in Fixed Cells for Super-Resolution Microscopy" *ChemBioChem*, 2017, pp. 1-9, vol. 18.

\* cited by examiner

Phage or virus display

Prokaryotic or eukaryotic cell display

Covalent capture phage or virus display

Covalent capture prokaryotic or eukaryotic cell display

SEQUENCE LISTING

```
Sequence total quantity: 48
SEQ ID NO: 1              moltype = AA  length = 340
FEATURE                   Location/Qualifiers
source                    1..340
                          mol_type = protein
                          organism = Streptococcus pyogenes
SEQUENCE: 1
MKLRHLLLTG AALTSFAATT VHGETVVNGA KLTVTKNLDL VNSNALIPNT DFTFKIEPDT   60
TVNEDGNKFK GVALNTPMTK VTYTNSDKGG SNTKTAEFDF SEVTFEKPGV YYYKVTEEKI  120
DKVPGVSYDT TSYTVQHVL WNEEQQKPVA TYIVGYKEGS KVPIQFKNSL DSTTLTVKKK  180
VSGTGGDRSK DFNFGLTLKA NQYYKASEKV MIEKTTKGGQ APVQTEASID QLYHFTLKDG  240
ESIKVTNLPV GVDYVVTEDD YKSEKYTTNV EVSPQDGAVK NIAGNSTEQE TSTDKDMTIT  300
FTNKKDFEVP TGVAMTVAPY IALGIVAVGG ALYFVKKKNA                        340

SEQ ID NO: 2              moltype = DNA  length = 1023
FEATURE                   Location/Qualifiers
source                    1..1023
                          mol_type = genomic DNA
                          organism = Streptococcus pyogenes
SEQUENCE: 2
atgaaattac gtcacttact attaacggga gcagccctaa ctagttttgc tgctacaaca   60
gttcacgggg agactgttgt aaacggagcc aaactaacag ttacaaaaaa ccttgattta  120
gttaatagca atgcattaat tccaaataca gattttacat ttaaaatcga acctgatact  180
actgtcaacg aagacggaaa taagtttaaa ggtgtagctt gaacacacc gatgactaaa  240
gtcacttaca ccaattcaga taaaggtgga tcaaatacga aaactgcaga atttgatttt  300
tcagaagtta cttttgaaaa accaggtgtt tattattaca agtaactga ggagaagata  360
gataaagttc ctggtgtttc ttatgataca acatctttca ctgttcaagt tcatgtcttg  420
tggaatgaag agcaacaaaa accagtagct acttatattg ttggttataa agaaggtagt  480
aaggtgccaa ttcagttcaa aaatagctta gattctacta cattaacggt gaagaaaaaa  540
gtttcaggta ccggtggaga tcgctctaaa gatttttaatt ttggtctgac tttaaaagca  600
aatcagtatt ataaggcgtc agaaaaagtc atgattgaga agacaactaa aggtggtcaa  660
gctcctgttc aaacagaggc tagtatagat caactctatc attttacctt gaaagatggt  720
gaatcaatca agtcacacaa tcttccagta ggtgtggatt atgttgtcac tgaagacgat  780
tacaaatcag aaaaatatac aaccaacgtg aagttagtc ctcaagatgg agctgtaaaa  840
aatatcgcag gtaattcaac tgaacaagag acatctactg ataaagatat gaccattact  900
tttacaaata aaaaagactt tgaagtgcca acaggagtag caatgactgt ggcaccatat  960
attgctttag gaattgtagc agttggtgga gctctttact tgttaaaaa gaaaaatgct 1020
taa                                                              1023

SEQ ID NO: 3              moltype = AA  length = 674
FEATURE                   Location/Qualifiers
source                    1..674
                          mol_type = protein
                          organism = Enterococcus faecalis
SEQUENCE: 3
MTKSVKFLVL LLVMILPIAG ALLIGPISFG AELSKSSIVD KVELDHTTLY QGEMTSIKVS   60
FSDKENQKIK PGDTITLTLP DALVGMTEND SSPRKINLNG LGEVFIYKDH VVATFNEKVE  120
SLHNVNGHFS FGIKTLITNS SQPNVIETDF GTATATQRLT IEGVTNTETG QIERDYPFFY  180
KVGDLAGESN QVRWFLNVNL NKSDVTEDIS IADRQGSGQQ LNKESFTFDI VNDKETKYIS  240
LAEFEQQGYG KIDFVTDNDF NLRFYRDKAR FTSFIVRYTS TITEAGQHQA TFENSYDINY  300
QLNNQDATNE KNTSQVKNVF VEGEASGNQN VEMPTEESLD IPLETIDEWE PKTPTSEQAT  360
ETSEKTDTTE TAESSQPEVH VSPTEEENPD EGETLGTIEP IIPEKPSVTT EENGTTETAE  420
SSQPEVHVSP TEEENPDESE TLGTIEPIIP EKPSVTTEEN GTTETAESSQ PEVHVSPAEE  480
ENPDESETLG TILPILPEKP SVTTEENGTT ETAESSQPEV HVSPTEEENP DESETLGTIA  540
PIIPEKPSVT TEENGITETA ESSQPEVHVS PTKEITTTEK KQPSTETTVE KNKNVTSKNQ  600
PQILNAPLNT LKNEGSPQLA PQLLSEPIQK LNEANGQREL PKTGTTKTPF MLIAGILAST  660
FAVLGVSYLQ IRKN                                                  674

SEQ ID NO: 4              moltype = DNA  length = 2025
FEATURE                   Location/Qualifiers
source                    1..2025
                          mol_type = genomic DNA
                          organism = Enterococcus faecalis
SEQUENCE: 4
atgacaaaaa gtgtaaaatt tttagtgtta ctgttggtaa tgattctacc aattgcgggg   60
gcgttattga ttggtccaat ttcgtttggc gccgaattga gcaaaagttc aatcgttgac  120
aaagtagaat tagatcacac tactttatat caaggagaga tgacctcaat taagtatctc  180
tttagtgaca aagaaaatca gaaaataaaa cctggagata ctattacttt aactttacca  240
gacgcactag ttggaatgac cgagaacgat agttcaccac gaaaaatcaa tttaaatggt  300
ttaggggaag ttttatctta taagatcat gttgtagcaa catttaacga aaaagttgaa  360
tctttacata atgtgaatgg gcattttttct ttcgggatta aaacgcttat caccaatagt  420
tctcaaccga atgtgataga aacggatttc ggaacagcaa cggcgactca acgtttgacg  480
attgaaggag tgactaacac agagactggc caaattgagc gagactatcc gtttttttat  540
aaagtaggcg atttggctgg agagtcaaat caagtacgtt ggtttttaaa tgtgaacctc  600
aataaatccg atgtcacaga agatatttca attgcggatc gacaaggaag tggtcaacaa  660
ttaaataaag agagttttac atttgatatt gtgaatgaca agaaactaa atatatttca  720
cttgccgagt ttgagcaaca aggttatggc aaaattgact cgtaacaga taatgacttt  780
aacttacgtt tttatcggga taagcacgc tttacttcct ttatcgtccg ttacacttcg  840
```

-continued

```
acaatcacag aagcaggcca acatcaagca acatttgaaa atagttatga catcaattat   900
caactaaaca atcaagacgc aacgaatgaa aaaaatacat cacaggttaa aaatgttttt   960
gtagaaggcg aggcaagcgg caatcaaaat gtggaaatgc caacagaaga aagtctagac  1020
attcctttag agacaataga tgaatgggaa ccaaagacac tacttcgga acaggcaaca  1080
gaaacaagtg aaaagacaga cacaacagaa accgcagaa gcagccaacc agaagttcat  1140
gtctcaccaa cagaagaaga aaatccagat gaaggtgaaa cactaggcac gattgagcca  1200
atcatacctg aaaaccaag tgtgacaact gaagagaatg gcacgacaga aactgcagaa  1260
agcagccaac cagaagttca tgtctcacca acagaagaag aaaatccaga tgaaagtgaa  1320
acactaggca cgattgagcc aatcatacct gaaaaaccaa gtgtgacaac tgaagagaa   1380
ggcacaacag aaaccgcaga aagcagccaa ccagaagttc atgtctcacc agcggaagaa  1440
gaaaatccag atgaaagtga aacgttaggt acaattttac caatcctacc tgaaaaacca  1500
agtgtgacaa ctgaagagaa tggcacaacg gaaactgcag aaagcagtca accagaagtc  1560
catgtgtcgc aacggaaga agaaaatcca gatgaaagtg aaacactagg cacgattgca  1620
ccaatcatac ctgaaaaacc aagcgtaaca actgaagaga atggtataac ggaaacgtca  1680
gaaagcagcc agccagaagt tcatgtctca ccaacaaaag aaattactac aactgagaaa  1740
aaacagccat ccacagaaac aactgtggag aaaaataaaa atgttacatc aaaaaatcaa  1800
ccacaaatac taaacgctcc attaaataca ttgaaaaatg aaggaagccc acagttggct  1860
ccccaactgc ttagtgaacc aattcaaaaa ttaaatgaaa caaacgggca acgagaactt  1920
cccaaaacag gcacaacaaa aacaccgttt atgctaatag caggaatact ggcaagtaca  1980
tttgccgttt aggtgtaag ttatctacaa atcagaaaga attaa                  2025

SEQ ID NO: 5            moltype = AA   length = 303
FEATURE                 Location/Qualifiers
source                  1..303
                        mol_type = protein
                        organism = Staphylococcus aureus
SEQUENCE: 5
GSARDISSTN VTDLTVSPSK IEDGGKTTVK MTFDDKNGKI QNGDMIKVAW PTSGTVKIEG    60
YSKTVPLTVK GEQVGQAVIT PDGATITFND KVEKLSDVSG FAEFEVQGRN LTQTNTSDDK   120
VATITSGNKS TNVTVHKSEA GTSSVFYYKT GDMLPEDTTH VRWFLNINNE KSYVSKDITI   180
KDQIQGGQQL DLSTLNINVT GTHSNYYSGQ SAITDFEKAF PGSKITVDNT KNTIDVTIPQ   240
GYGSYNSFSI NYKTKITNEQ QKEFVNNSQA WYQEHGKEEV NGKSFNHTVH NINANAGIEG   300
TVK                                                                303

SEQ ID NO: 6            moltype = AA   length = 102
FEATURE                 Location/Qualifiers
source                  1..102
                        mol_type = protein
                        organism = Streptococcus pyogenes
SEQUENCE: 6
MTIEEDSATH IKFSKRDIDG KELAGATMEL RDSSGKTIST WISDGQVKDF YLMPGKYTFV    60
ETAAPDGYEV ATAITFTVNE QGQVTVNGKA TKGDAHIVMV DA                     102

SEQ ID NO: 7            moltype = AA   length = 340
FEATURE                 Location/Qualifiers
source                  1..340
                        mol_type = protein
                        organism = Streptococcus pyogenes
SEQUENCE: 7
MKLRHLLLTG AALTSFAATT VHGETVVNGA KLTVTKNLDL VNSNALIPNT DFTFKIEPDT    60
TVNEDGNKFK GVALNTPMTK VTYTNSDKGG SNTKTAEFDF SEVTFEKPGV YYYKVTEEKI   120
DKVPGVSYDT TSYTVQVHVL WNEEQQKPVA TYIVGYKEGS KVPIQFKNSL DSTTLTVKKK   180
VSGTGGDRSK DFNFGLTLKA NQYYKASEKV MIEKTTKGGQ APVQTEASID QLYHFTLKDG   240
ESIKVTNLPV GVDYVVTEDD YKSEKYTTNV EVSPQDGAVK NIAGNSTEQE TSTDKDMTIT   300
FTNKKDFEVP TGVAMTVAPY IALGIVAVGG ALYFVKKKNA                         340

SEQ ID NO: 8            moltype = DNA   length = 1023
FEATURE                 Location/Qualifiers
source                  1..1023
                        mol_type = genomic DNA
                        organism = Streptococcus pyogenes
SEQUENCE: 8
atgaaattac gtcacttact attaacggga gcagccctaa ctagttttgc tgctacaaca    60
gttcacgggg agactgttgt aaacgggagcc aaactaacag ttacaaaaaa ccttgattta   120
gttaatagca atgcattaat tccaaataca gattttacat ttaaaatcga acctgatact   180
actgtcaacg aagacggaaa taagtttaaa ggtgtagctt tgaacacacc gatgactaaa   240
gtcacttaca ccaattcaga taaaggtgga tcaaatacga aaactgcaga atttgatttt   300
tcagaagtta cttttgaaaa accaggtgtt tattattaca agtaactaca ggaagaagata   360
gataaagttc ctggtgtttc ttatgataca tcatacaccgt gttcaagt tcatgtcttg   420
tggaatgaag agcaacaaaa accagtagct acttatattg ttggttataa agaaggtagt   480
aaggtgccaa ttcagttcaa aaatagctta gattctacta cattaacggt gaagaaaaaa   540
gtttcaggta ccggtggaga tcgctctaaa gatttaat ttggtctgac ttaaaagca    600
aatcagtatt ataaggcgtc agaaaaagtc atgattgaga gacaactaa aggtggtcaa   660
gctcctgtca aacagaggc tagtatagat caactctatc attttaccct gaaagatgat   720
gaatcaatca aagtcacaaa tcttccagta ggtgtggatt atgttgtcac tgaagacgat   780
tacaaatcag aaaaatatac aaccaacgtg aagttagtc ctcaagatgg agctgtaaaa   840
aatatcgcag gtaattcaac tgaacaagag acatctactg ataaagatat gaccattact   900
tttacaaata aaaaagactt tgaagtgcca acaggagtag caatgactgt ggcaccatat   960
attgctttag gaattgtagc agttggtgga gctctttact ttgttaaaaa gaaaaatgct  1020
```

```
                                          -continued
taa                                                                  1023

SEQ ID NO: 9           moltype = AA  length = 674
FEATURE                Location/Qualifiers
source                 1..674
                       mol_type = protein
                       organism = Enterococcus faecalis
SEQUENCE: 9
MTKSVKFLVL LLVMILPIAG ALLIGPISFG AELSKSSIVD KVELDHTTLY QGEMTSIKVS    60
FSDKENQKIK PGDTITLTLP DALVGMTEND SSPRKINLNG LGEVFIYKDH VVATFNEKVE   120
SLHNVNGHFS FGIKTLITNS SQPNVIETDF GTATATQRLT IEGVTNTETG QIERDYPFFY   180
KVGDLAGESN QVRWFLNVNL NKSDVTEDIS IADRQGSGQQ LNKESFTFDI VNDKETKYIS   240
LAEFEQQGYG KIDFVTDNDF NLRFYRDKAR FTSPIVRYTS TITEAGQHQA TFENSYDINY   300
QLNNQDATNE KNTSQVKNVF VEGEASGNQN VEMPTEESLD IPLETIDEWE PKTPTSEQAT   360
ETSEKTDTTE TAESSQPEVH VSPTEEENPD EGETLGTIEP IIPEKPSVTT EENGTTETAE   420
SSQPEVHVSP TEEENPDESE TLGTIEPIIP EKPSVTTEEN GTTETAESSQ PEVHVSPAEE   480
ENPDESETLG TILPILPEKP SVTTEENGTT ETAESSQPEV HVSPTEEENP DESETLGTIA   540
PIIPEKPSVT TEENGITETA ESSQPEVHVS PTKEITTTEK KQPSTETTVE KNKNVTSKNQ   600
PQILNAPLNT LKNEGSPQLA PQLLSEPIQK LNEANGQREL PKTGTTKTPF MLIAGILAST   660
FAVLGVSYLQ IRKN                                                    674

SEQ ID NO: 10          moltype = AA  length = 331
FEATURE                Location/Qualifiers
source                 1..331
                       mol_type = protein
                       organism = Staphylococcus aureus
SEQUENCE: 10
MNKNVLKFMV FIMLLNIITP LFNKNEAFAA RDISSTNVTD LTVSPSKIED GGKTTVKMTF    60
DDKNGKIQNG DMIKVAWPTS GTVKIEGYSK TVPLTVKGEQ VGQAVITPDG ATITFNDKVE   120
KLSDVSGFAE FEVQGRNLTQ TNTSDDKVAT ITSGNKSTNV TVHKSEAGTS SVFYYKTGDM   180
LPEDTTHVRW FLNINNEKSY VSKDITIKDQ IQGGQQLDLS TLNINVTGTH SNYYSGQSAI   240
TDFEKAFPGS KITVDNTKNT IDVTIPQGYG SYNSFSINYK TKITNEQQKE FVNNSQAWYQ   300
EHGKEEVNGK SFNHTVHNIN ANAGIEGTVK G                                 331

SEQ ID NO: 11          moltype = AA  length = 102
FEATURE                Location/Qualifiers
source                 1..102
                       mol_type = protein
                       organism = Streptococcus pyogenes
SEQUENCE: 11
MTIEEDSATH IKFSKRDIDG KELAGATMEL RDSSGKTIST WISDGQVKDF YLMPGKYTFV    60
ETAAPDGYEV ATAITFTVNE QGQVTVNGKA TKGDAHIVMV DA                     102

SEQ ID NO: 12          moltype = DNA  length = 309
FEATURE                Location/Qualifiers
source                 1..309
                       mol_type = genomic DNA
                       organism = Streptococcus pyogenes
SEQUENCE: 12
atgacaattg aagaagatag tgctacccat attaaattct caaaacgtga tattgacggc    60
aaaagagttag ctggtgcaac tatggagttg cgtgattcat ctggtaaaac tattagtaca   120
tggatttcag atggacaagt gaaagatttc tacctgatgc caggaaaata tacatttgtc   180
gaaaccgcag caccagacgg ttatgaggta gcaactgcta ttacctttac agttaatgag   240
caaggtcagg ttactgtaaa tggcaaagca actaaaggtg acgctcatat tgtcatggtt   300
gatgcttga                                                          309

SEQ ID NO: 13          moltype = AA  length = 893
FEATURE                Location/Qualifiers
source                 1..893
                       mol_type = protein
                       organism = Streptococcus pneumoniae
SEQUENCE: 13
MLNRETHMKK VRKIFQKAVA GLCCISQLTA FSSIVALAET PETSPAIGKV VIKETGEGGA    60
LLGDAVFELK NNTDGTTVSQ RTEAQTGEAI FSNIKPGTYT LTEAQPPVGY KPSTKQWTVE   120
VEKNGRTTVQ GEQVENREEA LSDQYPQTGT YPDVQTPYQI IKVDGSEKNG QHKALNPNPY   180
ERVIPEGTLS KRIYQVNNLD DNQYGIELTV SGKTVYEQKD KSVPLDVVIL LDNSNSMSNI   240
RNKNARRAER AGEATRSLID KITSDSENRV ALVTYASTIF DGTEFTVEKG VADKNGKRLN   300
DSLFWNYDQT SFTTNTKDYS YLKLTNDKND IVELKNKVPT EAEDHDGNRL MYQFGATFTQ   360
KALMKADEIL TQQARQNSQK VIFHITDGVP TMSYPINFNH ATFAPSYQNQ LNAFFSKSPN   420
KDGILLSDFI TQATSGEHTI VRGDGQSYQM FTDKTVYEKG APAAFPVKPE KYSEMKAAGY   480
AVIGDPINGG YIWLNWRESI LAYPFNSNTA KITNHGDPTR WYYNGNIAPD GYDVFTVGIG   540
INGDPGTDEA TATSFMQSIS SKPENYTNVT DTTKILEQLN RYFHTIVTEK KSIENGTITD   600
PMGELIDLQL GTDGRFDPAD YTLTANDGSR LENGQAVGGP QNDGGLLKNA KVLYDTTEKR   660
IRVTGLYLGT DEKVTLTYNV RLNDEFVSNK FYDTNGRTTL HPKEVEQNTV RDFPIPKIRD   720
VRKYPEITIS KEKKLGDIEF IKVNKNDKKP LRGAVFSLQK QHPDYPDIYG AIDQNGTYQN   780
VRTGEDGKLT FKNLSDGKYR LFENSEPAGY KPVQNKPIVA FQIVNGEVRD VTSIVPQDIP   840
AGYEFTNDKH YITNEPIPPK REYPRTGGIG MLPFYLIGCM MMGGVLLYTR KHP          893

SEQ ID NO: 14          moltype = DNA  length = 2682
```

| FEATURE | Location/Qualifiers |
|---|---|
| source | 1..2682 |
| | mol_type = genomic DNA |
| | organism = Streptococcus pneumoniae |

SEQUENCE: 14

```
atgctgaacc gcgaaaccca tatgaaaaaa gtaagaaaga tatttcgaa ggcagttgca    60
ggactgtgct gtatatctca gttgacagct ttttcttcga tagttgcttt agcagaaacg   120
cctgaaacca gtccagcgat aggaaaagta gtgattaagg agacaggcga aggaggagcg   180
cttctaggag atgccgtctt tgagttgaaa aacaatacga atggcacaac tgtttcgcaa   240
aggacagagg cgcaaaccgg agaagcgata ttttcaaaca taaaacctgg gacatacacc   300
ttgacagaag cccaacctcc agttggttat aaaccctcta ctaaacaatg gactgttgaa   360
gttgagaaga atggtcggac gactgtccaa ggtgaacagg tagaaaatcg agaagaggct   420
ctatctgacc agtatccaca aacagggact tatccagatg ttcaaacacc ttatcagatt   480
attaaggtag atggttcgga aaaaaacgga cagcacaagg cgttgaatcc gaatccatat   540
gaacgtgtga ttccagaagg tacactttca aagagaattt atcaagtgaa aatttggat   600
gataaccaat atggaatcga attgacggtt agtgggaaaa cagtgtatga acaaaaagat   660
aagtctgtgc cgctggatgt cgttatcttg ctcgataact caaatagtat gagtaacatt   720
cgaaacaaga atgctcgacg tgcggaaaga gctggtgagg cgcacgttc tcttattgat   780
aaaattacat ctgattcaga aaatagggta gcgcttgtga cttatgcttc cactatcttt   840
gatgggaccg agtttacagt agaaaaaggg gtagcagata aaacggaaa gcgattgaat   900
gattctcttt tttggaatta tgatcagacg agttttacaa ccaataccaa agattatagt   960
tatttaaagc tgactaataa taagaatgac atttgtagaat taaaaaaataa ggtacctacc  1020
gaggcagaag accatgatgg aaatagattg atgtaccaat tcggtgccac ttttactcag  1080
aaaagctttga tgaaggcaga tgagattttg acacaacaag cgagacaaaa tagtcaaaaa  1140
gtcatttttcc atattacgga tggtgtccca actatgtcgt atccgattaa ttttaatcat  1200
gctacgtttg ctccatcata tcaaaatcaa ctaaatgcat tttttagtaa atctcctaat  1260
aaagatggaa tactattaag tgattttatt acgcaagcaa ctagtggaga acatacaatt  1320
gtacgcggaa atgggcaaag ttaccagatg tttacagata agacagttta tgaaaaaggt  1380
gctcctgcag ctttcccagt taaacctgaa aaatattctg aaatgaaggc ggctggttat  1440
gcagttatag gcgatccaat taattggtga tatatttggc ttaattggga agagagtt   1500
ctggcttatc cgtttaattc taatactgct aaaattacca atcatggtga ccctacaaga  1560
tggtactata acgggaatat tgctcctgat gggtatgatg tctttacggt aggtattggt  1620
attaacggag atcctggtac ggatgaagca acggctacta gttttatgca agtatttct   1680
agtaaacctg aaaactatac caatgttact gacacgacaa aatattgga acagttgaat  1740
cgttatttcc acaccatcgt aactgaaaag aaatcaattg agaattggtac gattacagat  1800
ccgatgggtg agttaattga tttgcaattg ggcacagatg gaagatttga tccagcagat  1860
tacactttaa ctgcaaacga tggtagtcgc ttggagaatg gacaagctgt aggtggtcca  1920
caaaatgatg gtggtttgtt aaaaaatgca aaagtgctct atgatacgac tgagaaaagg  1980
attcgtgtaa caggtctgta ccttgaacg gatgaaaaag ttacgttgac ctacaatgtt  2040
cgtttgaatg atgagtttgt aagcaataaa ttttatgata ccaatggtcg aacaacctta  2100
catcctaagg aagtagaaca gaacacagtg cgcgacttcc cgattcctaa gattcgtgat  2160
gtgcggaagt atccagaaat cacaatttca aaagagaaaa aacttggtga cattgagttt  2220
attaaggtca ataaaaatga taaaaaacca ctgagaggtg ctgtctttag tcttcaaaaa  2280
caacatccgg attatccaga tatttatgga gctattgatc aaaatggcac ttatcaaaat  2340
gtgagaacag gtaagatgg taagttgacc tttaaaaatc tgtcagatgg aaatatcga   2400
ttatttgaaa attctgaacc agctggttat aaacccgttc aaaataagcc tatcgttgcc  2460
ttccaaatag taaatggaga agtcagagat gtgacttcaa tcgttccaca agatatacca  2520
gcgggttacg agtttacgaa tgataagcac tatattacca atgaacctat tcctccaaag  2580
agagaatatc ctcgaactgg tggtatcgga atgttgccat tctatctgat aggttgcatg  2640
atgatgggag gagttctatt atacacacgg aaacatccgt aa                      2682
```

| SEQ ID NO: 15 | moltype = AA length = 738 |
|---|---|
| FEATURE | Location/Qualifiers |
| source | 1..738 |
| | mol_type = protein |
| | organism = Streptococcus intermedius |

SEQUENCE: 15

```
MKKRRGQFFK SAISFLVVFL MVMVSIIYPS SKIKADGFPN DATGVSPNGK YYSAGRENRL    60
GMVTSDELHT ATELFGFCMA NSKKYPGYDS KKDEYFGVYE QILNLNKESF NKLVRDNHTY   120
GNIPTSPEEL WDKVSKLIYI YLKDPTNVIG QAGWTNPQDA MYEFYTVVQQ EIWRYTDGQK   180
VDKDTNSYLY YKYSKQGQKA VYLLRDAVNS ISIPSNFELR GYKPEWVQGQ KGYQAIVTGR   240
LKVDQPVGEI KTTVTAGGKT SSENDIATLK AQDVIGGVEV SDKITYSGLY PNTEYDVIGE   300
IYEVKDGELV NPGRPVSVVN SGDDLKTDAT GKGKWTLNLK KLDLEAGKSY VVFEKVVSLK   360
NVIDTDGDGK PDKKQELSHN DPKDKSQTFT ILPKEIVEQD VVFSKVNVAG EEIAGAKIQL   420
KDAQGQVVHS WTSKAGQSET VKLKAGTYTF HEASAPTGYL AVTDITFEVD VQGKVTVKDA   480
NGNGVKADGN KLTVTDQAAP SVPNEQDVVF SKVNVAGEEI AGAKIQLKDA QGQVVHSWTS   540
KAGQSETVKL KAGTYTFHEA SAPTGYLAVT DITFEVDVQG KVTVKDANGN GVKADGNKLT   600
VTDQAAPSVP NEQDVVFSKV NVAGEEIAGA KIQLKDAQGQ VVHSWTSKAG QSETVKLKAG   660
TYTFHEASAP TGYLAVTDIT FEVDVQGKVT VKDANGNGVK ADGNKLTVTD QAAPSVPNEQ   720
DVVFSKVNVA GEEIAGAK                                                  738
```

| SEQ ID NO: 16 | moltype = DNA length = 2215 |
|---|---|
| FEATURE | Location/Qualifiers |
| source | 1..2215 |
| | mol_type = genomic DNA |
| | organism = Streptococcus intermedius |

SEQUENCE: 16

```
atgaaaaaga gaagaggaca atttttcaaa agtgcaattt cgttttggt tgtatttttg    60
atggtaatgg taagtatcat ttaccatctc tcaaaaatta agcagatgg atttcctaat   120
```

-continued

```
gatgctacgg gagtatcgcc aaatggtaaa tattactcgg cagggagaga aaaccgttta   180
ggaatggtta catcagatga attgcataca gctacagaat tattcggttt ttgtatggca   240
aatagcaaga aatatccagg atatgattca aaaaaggatg agtatttttgg ggtgtatgaa   300
caaatcttaa accttaataa agaaagcttt aataagcttg ttagagataa tcatacgtat   360
ggtaacattc ctacaagtcc agaggaactt tgggataaaa tatctaaact gatttatatt   420
tatttgaaag accctacaaa tgttattgga caagctgggt ggacgaatcc acaggatgca   480
atgtatgaat tttatactgt tgtacaacag gaaatatggc gttatacaga tggacaaaag   540
gtggataaag acaccaattc atatttgtat tataaatatt caaaacaagg tcaaaaagca   600
gtgtacttac tgcgtgacgc tgtgaatagc atcagtatac ctagtaatt tgaacttcgt    660
ggctataaac ctgaatgggt tcaaggtcaa aaaggatacc aagctattgt aactggtaga   720
ttgaaagtag atcaacctgt cggggaaata aagactacag taacagcagg tggaaaaacc   780
tcaagtgaaa acgacattgc tacattgaag gcgcaagacg ttataggtgg ggttgaagtc   840
tctgataaga taacatatag tggtctttat ccaaatacga aatatgatgt tataggtgaa   900
atttacgaag taaaagatgg agaacttgtt aatccaggac gaccggtttc tgtagtcaat   960
agtggtgacg atttaaaaac agatgcaaca ggaaaaggga aatggacatt aaactttgga  1020
aagcttgatt tagaagcagg aaaatcctat gtggtctttg aaaagttgt ttcattaaaa   1080
aacgtgatag atacagatgg agatggaaaa ccggataaaa aacaagaact atcgcataat  1140
gatccaaaag ataaatcgca aacattacca attttaccta aggaaatagt tgaacaagac  1200
gttgtcttca gtaaggtgaa tgtggctggt gaagaaatcg ctggtgcgaa gatccaactg  1260
aaggatgcgc aaggtcaagt tgttcattcc tggacttcta aagcgggtca aagtgaaacg  1320
gtcaaattga aagctggcac ctatactttc catgaagcat ccgctccgac tggttacttg  1380
gccgtaacgg atatcacatt cgaagtagat gttcaaggaa aagtgacgcc taaggatgcc  1440
aacggcaatg gtgttaaggc ggatggtaat aagttaacgg tgaccgatca agctgctcct  1500
agcgtaccga atgaacaaga cgttgtcttc agtaaggtga atgtgctggt gaagaaatc   1560
gctggtgcga agatccaact gaaggatgcg caaggtcaag ttgttcattc ctggacttct  1620
aaagcgggtc aaagtgaaac ggtcaaattg aaagctggca cctatacttt ccatgaagca  1680
tccgctccga ctggttactt ggccgtaacg gatatcacat tcgaagtaga tgttcaagga  1740
aaagtgacgg ttaaggatgc caacggcaat ggtgttaagg cggatggtaa taagttaacg  1800
gtgaccgatc aagctgctcc tagcgtaccg aatgaacaag acgttgtctt cagtaaggtg  1860
aatgtggctg gtgaagaaat cgctggtgcg aagatccaac tgaaggatgc gcaaggtcaa  1920
gttgttcatt cctggacttc taaagcgggt caaagtgaaa cggtcaaatt gaaagctggc  1980
acctatactt tccatgaagc atccgctccg actggttact tggccgtaac ggatatcaca  2040
ttcgaagtag atgttcaagg aaaagtgacg gttaaggatg ccaacggcaa tggtgttaag  2100
gcggatggta taagttaac ggtgaccgat caagctgctc ctagcgtacc gaatgaacaa   2160
gacgttgtct tcagtaaggt gaatgtgctt ggtgaagaaa tcgctggtgc gaaga        2215
```

SEQ ID NO: 17        moltype = AA   length = 5
FEATURE              Location/Qualifiers
REGION               1..5
                     note = synthetic
SITE                 3
                     note = MISC_FEATURE - X is any amino acid
source               1..5
                     mol_type = protein
                     organism = synthetic construct
SEQUENCE: 17
LPXTG                                                                5

SEQ ID NO: 18        moltype = AA   length = 6
FEATURE              Location/Qualifiers
REGION               1..6
                     note = synthetic
source               1..6
                     mol_type = protein
                     organism = synthetic construct
SEQUENCE: 18
LPTGAA                                                               6

SEQ ID NO: 19        moltype = AA   length = 6
FEATURE              Location/Qualifiers
REGION               1..6
                     note = Synthetic
source               1..6
                     mol_type = protein
                     organism = synthetic construct
SEQUENCE: 19
LPTGGG                                                               6

SEQ ID NO: 20        moltype = AA   length = 6
FEATURE              Location/Qualifiers
REGION               1..6
                     note = synthetic
source               1..6
                     mol_type = protein
                     organism = synthetic construct
SEQUENCE: 20
LPKTGG                                                               6

SEQ ID NO: 21        moltype = AA   length = 5

```
FEATURE                 Location/Qualifiers
REGION                  1..5
                        note = synthetic
source                  1..5
                        mol_type = protein
                        organism = synthetic construct
SEQUENCE: 21
LPETG                                                                           5

SEQ ID NO: 22           moltype = AA  length = 5
FEATURE                 Location/Qualifiers
REGION                  1..5
                        note = synthetic
SITE                    3
                        note = MISC_FEATURE - X is any amino acid
source                  1..5
                        mol_type = protein
                        organism = synthetic construct
SEQUENCE: 22
LPXTG                                                                           5

SEQ ID NO: 23           moltype = AA  length = 6
FEATURE                 Location/Qualifiers
REGION                  1..6
                        note = synthetic
SITE                    3
                        note = MISC_FEATURE - X is any amino acid
SITE                    6
                        note = MISC_FEATURE - X is any amino acid
source                  1..6
                        mol_type = protein
                        organism = synthetic construct
SEQUENCE: 23
LPXTGX                                                                          6

SEQ ID NO: 24           moltype =    length =
SEQUENCE: 24
000

SEQ ID NO: 25           moltype = AA  length = 40
FEATURE                 Location/Qualifiers
REGION                  1..40
                        note = synthetic
source                  1..40
                        mol_type = protein
                        organism = synthetic construct
SEQUENCE: 25
MGSSHHHHHH SSGLVPRGSV PTIVMVDAYK RYKGSGESGK                                     40

SEQ ID NO: 26           moltype = AA  length = 139
FEATURE                 Location/Qualifiers
REGION                  1..139
                        note = synthetic
source                  1..139
                        mol_type = protein
                        organism = synthetic construct
SEQUENCE: 26
MSYYHHHHHH DYDIPTTENL YFQGAMVTTL SGLSGEQGPS GDMTTEEDSA THIKFSKRDE               60
DGRELAGATM ELRDSSGKTI STWISDGHVK DFYLYPGKYT FVETAAPDGY EVATAITFTV              120
NEQGQVTVNG EATKGDAHT                                                          139

SEQ ID NO: 27           moltype = AA  length = 15
FEATURE                 Location/Qualifiers
REGION                  1..15
                        note = synthetic
source                  1..15
                        mol_type = protein
                        organism = synthetic construct
SEQUENCE: 27
VPTIVMVDAY KRYKS                                                               15

SEQ ID NO: 28           moltype = AA  length = 119
FEATURE                 Location/Qualifiers
REGION                  1..119
                        note = synthetic
source                  1..119
                        mol_type = protein
                        organism = synthetic construct
SEQUENCE: 28
```

```
YFQGAMVTTL SGLSGEQGPS GDMTTEEDSA THIKFSKRDE DGRELAGATM ELRDSSGKTI    60
STWISDGHVK DFYLYPGKYT FVETAAPDGY EVATAITFTV NEQGQVTVNG EATKGDAHT    119

SEQ ID NO: 29           moltype = DNA   length = 1689
FEATURE                 Location/Qualifiers
misc_feature            1..1689
                        note = exemplary SpyCatcher-pIII sequence
misc_feature            1..6
                        note = EcoRI (2)
misc_feature            7..63
                        note = DsbA signal peptide
misc_feature            64..411
                        note = SpyCatcher
misc_feature            412..432
                        note = TEV cleavage site
misc_feature            433..468
                        note = Linker
misc_feature            463..468
                        note = XbaI
misc_feature            469..1686
                        note = gIII
source                  1..1689
                        mol_type = other DNA
                        organism = synthetic construct
SEQUENCE: 29
gaattcatga agaagatctg gttagcgtta gctggtcttg tgttggcgtt tagtgctagt    60
gccggggcaa tggtggacac gttgtcaggt ctgagctcag aacagggtca gtcgggtgat    120
atgaccattg aggaagatag cgcaacccac atcaaattta gcaagcgcga tgaagatggc    180
aaagagcttg ccggcgcgac aatggagtta cgggattctt ccggcaagac cattagcacc    240
tggatttccg atggccaggt aaaagacttc tatctgtatc cgggaaaata cccttttgtc    300
gaaacggctg cacctgacgg ctatgaggtt gcaaccgcca tcacattcac ggttaacgaa    360
cagggtcagt aaccgtcaa tggcaaagcg actaaaggcg atgcgcatat tgagaatctg    420
tactttcaag gcgcggaggc gggtctggc ggtggtggtt cgtctagagc tgaaactgtt    480
gaaagttgtt tagcaaaacc ccatacagaa aattcattta ctaacgtctg gaaagacgac    540
aaaactttag atcgttacgc taactatgag gctgtctgt ggaatcatcaa aggcgttgta    600
gtttgtactg gtgacgaaac tcagtgttac ggtacatggg ttcctattgg gcttgctatc    660
cctgaaaatg aggggtggtgg ctctgagggt ggcggttctg agggtggcgg ttctgagggt    720
ggcggtacta aacctcctga gtacggtgat acacctattc cgggctatac ttatatcaac    780
cctctccgacg gcacttatcc gcctggtact gagcaaaacc cctaatcc taatccttct    840
cttgaggagt ctcagcctct taatactttc atgtttcaga ataataggtt ccgaaatagg    900
cagggggcat taactgttta cgggcact gttactcaag gcactgaccc cgttaaaact    960
tattaccagt acactcctgt atcatcaaaa gccatgtatg acgcttactg gaacggtaaa    1020
ttcagagact gcgcttttca ttctgcgtttt aatgaggatc cattcgtttg tgaatatcaa    1080
ggccaatcgt ctgacctgcc tcaacctcct gtcaatgctg gcggcggctc tggtggtggt    1140
tctggtggcg gctctgaggg tggtggctct gagggtggcg gttctgaggg tggcggctct    1200
gagggaggcg gttccggtgg tggctctggt tccggtgatt ttgattatga aaagatggca    1260
aacgctaata agggggctat gaccgaaaat gccgatgaaa acgcgctaca gtctgacgct    1320
aaaggcaaac ttgattctgt cgctactgat tacggtgctg ctatcgatgg tttcattggt    1380
gacgtttccg gccttgctaa tggtaatggt gctactggtg attttgctgg ctctaattcc    1440
caaatggctc aagtcggtga cggtgataat tcacctttaa tgaataattt ccgtcaatat    1500
ttaccttccc tccctcaatc ggttgaatgt cgcccttttg tctttggcgc tggtaaacca    1560
tatgaattttt ctattgattg tgacaaaata aacttattcc gtggtgtctt tgcgtttctt    1620
ttatatgttg ccacctttat gtatgtattt tctacgtttg ctaacatact gcgtaataag    1680
gagtcttaa                                                           1689

SEQ ID NO: 30           moltype = AA   length = 562
FEATURE                 Location/Qualifiers
REGION                  1..562
                        note = Synthetic Construct
source                  1..562
                        mol_type = protein
                        organism = synthetic construct
SEQUENCE: 30
EFMKKIWLAL AGLVLAFSAS AGAMVDTLSG LSSEQGQSGD MTIEEDSATH IKFSKRDEDG    60
KELAGATMEL RDSSGKTIST WISDGQVKDF YLYPGKYTFV ETAAPDGYEV ATAITFTVNE    120
QGQVTVNGKA TKGDAHIENL YFQGGGGGSG GGSSRAETV ESCLAKPHTE NSFTNVWKDD    180
KTLDRYANYE GCLWNATGVV VCTGDETQCY GTWVPIGLAI PENEGGGSEG GGSEGGGSEG    240
GGTKPPEYGD TPIPGYTYIN PLDGTYPPGT EQNPANPNPS LEESQPLMTF MFQNNRFRNR    300
QGALTVYTGT VTQGTDPVKT YYQYTPVSSK AMYDAYWNGK FRDCAFHSGF NEDPFVCEYQ    360
GQSSDLPQPP VNAGGGSGGG SGGGSEGGGS EGGGSEGGGS EGGGSGGGSG SGDFDYEKMA    420
NANKGAMTEN ADENALQSDA KGKLDSVATD YGAAIDGFIG DVSGLANGNG ATGDFAGSNS    480
QMAQVGDGDN SPLMNNFRQY LPSLPQSVEC RPFVFGAGKP YEFSIDCDKI NLFRGVFAFL    540
LYVATFMYVF STFANILRNK ES                                            562

SEQ ID NO: 31           moltype =   length =
SEQUENCE: 31
000

SEQ ID NO: 32           moltype = AA   length = 4
```

```
FEATURE              Location/Qualifiers
REGION               1..4
                     note = sortase B bridging domain
source               1..4
                     mol_type = protein
                     organism = synthetic construct
SEQUENCE: 32
GGGG                                                                     4

SEQ ID NO: 33        moltype = AA  length = 10
FEATURE              Location/Qualifiers
REGION               1..10
                     note = linker
source               1..10
                     mol_type = protein
                     organism = synthetic construct
SEQUENCE: 33
GGGGSGGGGS                                                              10

SEQ ID NO: 34        moltype = AA  length = 13
FEATURE              Location/Qualifiers
REGION               1..13
                     note = SpyTag
source               1..13
                     mol_type = protein
                     organism = synthetic construct
SEQUENCE: 34
AHIVMVDAYK PTK                                                          13

SEQ ID NO: 35        moltype = AA  length = 16
FEATURE              Location/Qualifiers
REGION               1..16
                     note = SpyTag variant
source               1..16
                     mol_type = protein
                     organism = synthetic construct
SEQUENCE: 35
PPVPTIVMVD AYKPTK                                                       16

SEQ ID NO: 36        moltype = AA  length = 16
FEATURE              Location/Qualifiers
REGION               1..16
                     note = SpyTag variant
source               1..16
                     mol_type = protein
                     organism = synthetic construct
SEQUENCE: 36
RPCYVIVMVD AYKPTK                                                       16

SEQ ID NO: 37        moltype = AA  length = 16
FEATURE              Location/Qualifiers
REGION               1..16
                     note = SpyTag variant
source               1..16
                     mol_type = protein
                     organism = synthetic construct
SEQUENCE: 37
GRYAWIVMVD AYKPTK                                                       16

SEQ ID NO: 38        moltype = AA  length = 13
FEATURE              Location/Qualifiers
REGION               1..13
                     note = SpyTag variant
source               1..13
                     mol_type = protein
                     organism = synthetic construct
SEQUENCE: 38
VPTIVMVDCY KRY                                                          13

SEQ ID NO: 39        moltype = AA  length = 13
FEATURE              Location/Qualifiers
REGION               1..13
                     note = SpyTag variant
source               1..13
                     mol_type = protein
                     organism = synthetic construct
SEQUENCE: 39
VPTIVMVDCC LFC                                                          13
```

```
SEQ ID NO: 40          moltype = AA   length = 13
FEATURE                Location/Qualifiers
REGION                 1..13
                       note = SpyTag variant
source                 1..13
                       mol_type = protein
                       organism = synthetic construct
SEQUENCE: 40
VPTIVMVDFW MRC                                                        13

SEQ ID NO: 41          moltype = AA   length = 13
FEATURE                Location/Qualifiers
REGION                 1..13
                       note = SpyTag variant
source                 1..13
                       mol_type = protein
                       organism = synthetic construct
SEQUENCE: 41
VPTIVMVDCR LDS                                                        13

SEQ ID NO: 42          moltype = AA   length = 13
FEATURE                Location/Qualifiers
REGION                 1..13
                       note = SpyTag variant
source                 1..13
                       mol_type = protein
                       organism = synthetic construct
SEQUENCE: 42
VPTIVMVDCQ LAS                                                        13

SEQ ID NO: 43          moltype = AA   length = 13
FEATURE                Location/Qualifiers
REGION                 1..13
                       note = SpyTag variant
source                 1..13
                       mol_type = protein
                       organism = synthetic construct
SEQUENCE: 43
VPTIVMVDCS LSP                                                        13

SEQ ID NO: 44          moltype = AA   length = 13
FEATURE                Location/Qualifiers
REGION                 1..13
                       note = SpyTag variant
source                 1..13
                       mol_type = protein
                       organism = synthetic construct
SEQUENCE: 44
VPTIVMVDPY QGT                                                        13

SEQ ID NO: 45          moltype = AA   length = 13
FEATURE                Location/Qualifiers
REGION                 1..13
                       note = SpyTag variant
source                 1..13
                       mol_type = protein
                       organism = synthetic construct
SEQUENCE: 45
VPTIVMVDYP SRC                                                        13

SEQ ID NO: 46          moltype = AA   length = 13
FEATURE                Location/Qualifiers
REGION                 1..13
                       note = SpyTag variant
source                 1..13
                       mol_type = protein
                       organism = synthetic construct
SEQUENCE: 46
VPTIVMVDCY KRY                                                        13

SEQ ID NO: 47          moltype = AA   length = 13
FEATURE                Location/Qualifiers
REGION                 1..13
                       note = SpyTag variant
source                 1..13
                       mol_type = protein
                       organism = synthetic construct
SEQUENCE: 47
VPTIVMVDFI LAN                                                        13
```

```
SEQ ID NO: 48          moltype = AA  length = 14
FEATURE                Location/Qualifiers
REGION                 1..14
                       note = SpyTag variant
source                 1..14
                       mol_type = protein
                       organism = synthetic construct
SEQUENCE: 48
VPTIVMVDAY KRYK                                                              14
```

DISPLAY SYSTEMS FOR PROTEINS OF INTEREST

The Sequence Listing for this application is labeled "Seq-List.xml" which was created on Sep. 19, 2022 and is 72,656 bytes. The entire content of the sequence listing is incorporated herein by reference in its entirety.

BACKGROUND OF THE INVENTION

Phage Display

Selection of proteins with specific properties from large libraries is a well-established process. Phage display is the oldest and most commonly used selection method. It is based on the presentation of the protein of interest (POI) on the surface of phages which contain the corresponding DNA of the POI, for example, an antibody. For phage display, the POI is covalently linked to a phage coat protein. Most frequently, a genetic fusion to the gene III protein (pIII) of filamentous phage M13 is used but fusions to the other coat proteins have been in the literature as well. The POI-pIII fusion is usually cloned into a phagemid vector which contains an antibiotic resistance marker, origins of replication for phage and bacterial DNA polymerases, and a phage morphogenetic signal for the packaging of the phagemid into the phage (Qi et al., 2012).

The missing genes for phage production are supplied by infection with a helper phage, a full-length phage with a mutated packaging signal. Due to this mutation, predominantly the phagemid, and not the helper phage DNA, is packaged into the phage coat. These phages typically contain only one POI-pIII fusion on the surface since the wild-type pIII from the helper phage is incorporated faster than the fusion protein from the phagemid. The resulting monovalent protein display allows the selection for protein binding strength as it is not influenced by any avidity effects. Multivalent display can be achieved by using hyperphage, a modified helper phage which does not contain a wild-type geneIII (gIII), therefore, all 5 copies of pIII have to originate from the phagemid (Rondot et al., 2001).

Instead of a genetic fusion between POI and pIII, it is also possible to connect the POI to the phage via a disulfide bond. In this system termed CysDisplay®, the pIII on the phagemid carries a cysteine at the N-terminus, and the POI has an additional cysteine at the C-terminus of the heavy chain (Rothe et al., 2008). Upon export to the periplasm, they form a disulfide bond and are incorporated into the phage coat. The advantage of CysDisplay® is the simple and quantitative elution of the specific phage POIs by cleavage of the disulfide bond with a reducing agent like DTT, a method that is independent of POI affinity. This avoids bias towards low-affinity POI, which are more readily eluted by conventional pH shift elution. A similar advantage can be achieved by a genetic fusion containing a protease cleavable linker (Ward et al., 1996).

Non-covalent ways to display a POI on the pIII protein are the use of two dimerization domains (Wang et al., 2010) or the protein A ZZ domain (Mazor et al., 2010).

In phage display, selection is performed for typically 2 to 4 rounds to enrich clones that contain the desired properties like binding to a target or enzymatic activity. The selection output is then screened to identify the desired clones. For this step, the POI are usually expressed without the pIII most commonly by subcloning into an expression vector, by removing the gene III from the vector by restriction digest and re-ligation or by using an amber stop codon between the POI and the gIII in combination with *E. coli* strains lacking suppressor tRNAs. However, for expression of larger amounts, the POI is usually subcloned into an expression vector which gives higher yields than the amber stop codon system. This subcloning step is a laborious and time consuming step especially for high throughput selections against a multitude of targets in parallel.

Protein Ligation

Several technologies have been developed in recent years that enable covalent conjugation of polypeptides at specific pre-determined sites. One example is the sortase system (Schmohl et al., 2014), whereby a short peptide (the sorting motif) is genetically fused to the C-terminus of one polypeptide and two glycine residues are genetically fused to the N-terminus of a second peptide (or vice versa). In the presence of the sortase enzyme, the two modified polypeptides are fused together. A disadvantage of this system is the slow enzymatic reaction and the relatively low yield of end product that can be currently achieved. Other enzymatic protein ligase systems are butelase (Nguyen et al., 2014) or peptiligase (Toplak et al., 2016).

Another example is the in-frame addition of nucleotides encoding one or more cysteines to the C- or N termini of two polypeptides. When such free cysteine containing polypeptides are mixed under oxidizing conditions, they will form disulfide bridges. Such systems, however, suffer from the many side-products that will appear.

A third example is the so-called SpyTag/SpyCatcher (Reddington et al., 2015) system. Here, the concept of spontaneous isopeptide formation in naturally occurring proteins has been used to covalently attach one polypeptide to another. A domain from the *Streptococcus pyogenes* protein FbaB that contains such an isopeptide bond has been split into two parts. One part, the SpyTag, is a 13 amino acid peptide that contains part of the autocatalytic center. The other part, the SpyCatcher, is a 116 amino acid protein domain containing the other part of the center. It was shown that mixing those two polypeptides restores the autocatalytic center and leads to formation of the isopeptide bond, thereby covalently bind the SpyTag to the SpyCatcher (Zakeri et al., 2012). Further engineering has led to a shorter version of SpyCatcher with only 84 amino acids as well as an optimized version, SpyTag002 and SpyCatcher002 with accelerated reaction (Keeble et al., 2017; which is hereby incorporated by reference in its entirety). A further modification of the system was the invention of SpyLigase (Fierer et al., 2014), which was achieved by splitting the FbaB domain into three parts, the SpyTag, the K-tag and the SpyLigase. SpyTag and K-tag are both short peptides that are covalently fused by addition of SpyLigase.

BRIEF DESCRIPTION OF THE FIGURES

FIG. 2 provides an exemplary SpyCatcher-pIII sequence (SEQ ID NOs: 29 and 30).

FIG. 3A shows detection with anti-SpyCatcher antibody which can only detect the modified SpyCatcher phage but not the VCSM13 phage. FIG. 3*b* shows a Western blot with anti-pIII detection which gives a signal for both phages but shows a larger product (SpyCatcher-pIII fusion) for the SpyCatcher phages.

BRIEF DESCRIPTION OF THE INVENTION

Figure 1A:
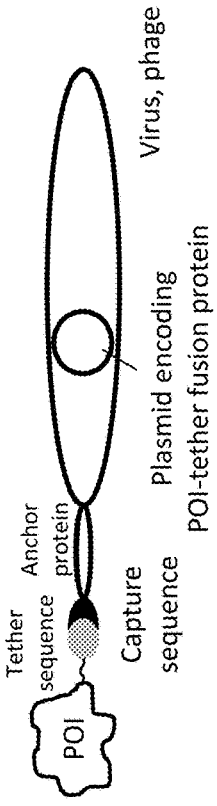
FIGS. 1A-1D provide an illustration of the phage and cell display (FIGS. 1A-1B) and the disclosed invention (FIGS. 1C-1D).
Figure 1B:
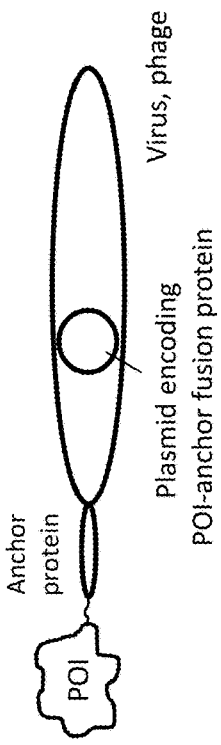
Figure 1C:
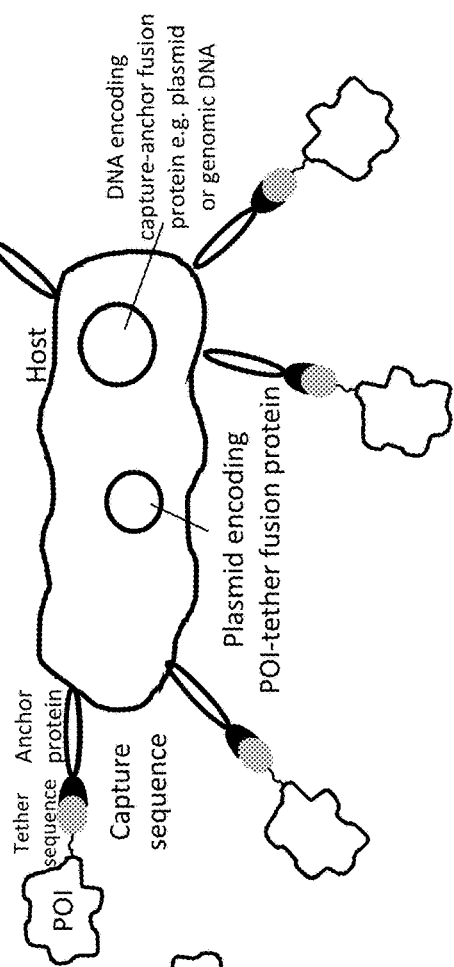
Figure 1D:
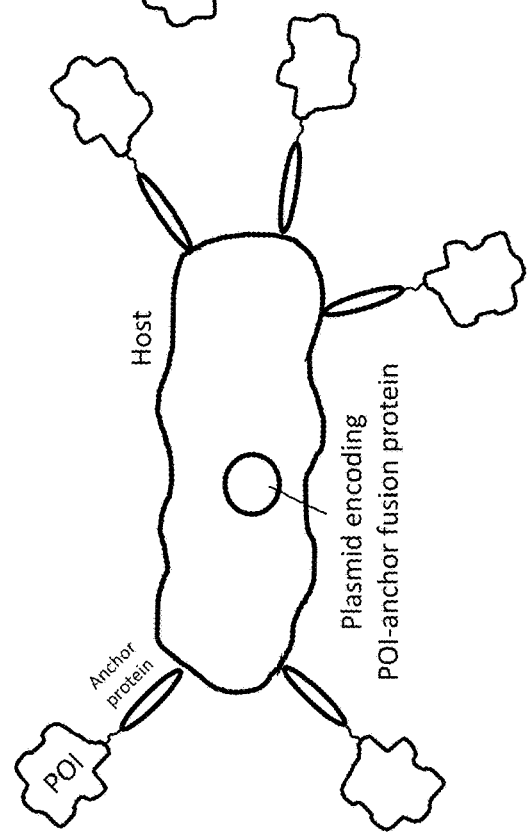

The invention described herein is a protein display selection method which uncouples the POI library from the display selection system. This is achieved by removing the fusion partner (e.g. gIIII protein in the case of phage display) from the library vector. Display of the POI can be achieved by forming a covalent bond between the POI and the anchor protein post expression either by enzymatic protein ligation (e.g. SpyLigase, SnoopLigase, sortase, butelase, peptiligase etc.) or by spontaneous covalent bond formation (e.g. SpyTag/SpyCatcher, SnoopTag/SnoopCatcher, etc.). The POI library is fused to a tethering sequence, for example SpyTag, at the C-terminus of the POI which then forms a covalent bond to a capture sequence found on an anchor protein, for example, the SpyCatcher-fused anchor protein, e.g., a SpyCatcher-geneIII protein (SpyCatcher-pIII) fusion, for the most common form of phage display. Alternatively, the POI is fused to the capture protein and the anchor protein is fused to the tether sequence. FIG. 1 provides a schematic representation of the disclosed invention.

To keep the library separate from the anchor protein, the capture-anchor protein gene is not encoded on the library phagemid but either by a modified helper phage, modified *E. coli* genome or an additional plasmid—for phage display or bacterial display—or by a modified expression host or additional plasmid for other display techniques.

The display system of this invention expresses the POI for the selection steps without modification i.e. without fusion to an anchor protein. Therefore, the expressed POI during selection is identical to the protein used for the following screening and production steps. Circumventing an artificial fusion (e.g., POI-pIII), which is required in conventional display selection systems, can avoid a bias in the selection introduced by different properties (expression, solubility, activity, stability, etc.) of a POI-anchor fusion protein. Furthermore, since the POI is not expressed as an anchor fusion protein, no subcloning step is required prior to screening and expression. This saves time and effort especially in high throughput selection settings.

By keeping the library vector independent from the selection system, the library becomes usable for various display selection systems i.e. different coat proteins for phage display (coat proteins other than pIII) as well as other display systems (e.g., yeast display, mammalian or bacterial display) as long as the vector elements are compatible with the other host. The development of dual host vectors for switching from prokaryotic to eukaryotic expression systems have been described (e.g. Tesar et al. 2013, Batonick et al. 2016). The display system can also be switched within a selection between different selection rounds or after selection for screening e.g. of POI displayed on other hosts.

For phage display a high display rate of the POI on the phage is often beneficial in the first selection round. In standard phage display this can be achieved by using hyperphage without a gIII leaving the POI-pIII as the only source for pIII and thus producing phage with several POI on the phage surface. In the invention described here, a high display rate can be achieved by infecting *E. coli* containing the POI library with a modified helper phage which carries a SpyCatcher-gIII instead of gIII All copies of the pIII in the phage coat thus carry a SpyCatcher which enables protein ligation of several POI per phage. To achieve a monovalent display in the following rounds, to select for affinity rather than avidity, the selected phages of the first round are used to infect a modified *E. coli* strain which carries a SpyCatcher-gIII fusion in their genome or carries an additional plasmid for co-expression of SpyCatcher-gIII The SpyCatcher can be fused to a complete gIII (N1-N2-Ct) or to truncated or modified gIII (N2-Ct or Ct). After infection with helper phage, bacteria produce new phages which predominantly carry the wildtype pIII from the helper phage as it gets incorporated into the phage coat faster than the modified pIII from the *E. coli* genome/second plasmid. Alternatively, an additional SpyTag or a SpyTag fusion protein can be co-expressed which competes with the POI-SpyTag fusion for ligation with SpyCatcher which is introduced by the modified SpyCatcher-pIII helper phage. Instead of gIII other phage coat proteins can be used.

After the last selection round, non-modified *E. coli* which do not carry a SpyCatcher-fusion gene are infected with the phage output and can be used for screening and expression. The SpyTag at the C-terminus of the POI can be used for detection (with appropriate antibodies against the tag) as well as for conjugation with biotinylated, fluorescent- or enzyme-labeled SpyCatcher.

Thus, one embodiment of the envisioned invention consists of the POI-SpyTag fusion protein and the SpyCatcher-phage coat protein fusion, either produced by a modified *E. coli* strain, by a modified helper phage or co expressed by a second plasmid to display POI on the surface of phage.

In one embodiment, a POI-tethering sequence fusion protein is linked to a capture sequence-anchor fusion protein to display the POI on the surface of a biological entity. The capture sequence-anchor protein fusion is part of, or associated with, the outer surface of the biological entity and thus links the POI to the surface of the biological entity by formation of a covalent bond between the tethering sequence and the capture sequence. Furthermore, the biological entity contains the DNA which encodes the POI and thus provides a physical link of the POI and its DNA which is required for protein selection systems. In one non-limiting embodiment, the biological entity can be a phage with the capture sequence fused to a phage coat protein such as pIII-, pVI-, pVII-, pVIII- or pIX protein or an optimized, modified or truncated version of these coat proteins and the phagemid encoding the POI inside the phage coat. In other embodiments, the biological entity can be a yeast e.g., *Saccharomyces cerevisiae* or *Pichia pastoris* with the capture sequence fused to, e.g., the a-agglutinin yeast adhesion receptor, a bacteria or a mammalian cell. The POI can be a protein or a library of proteins such as antibodies, antibody fragments, single chain antibodies (e.g., scFv, scFab), single domain antibodies, protein scaffolds (e.g., based on fibronectin III, cystatin, lipocalins, Ankyrin repeat domains, Z domain of protein A and others) etc. The system can be used to select for proteins with certain properties such as affinity, activity or certain biological or physical properties. Depending on the biological entity the selection system would be referred to as phage display, yeast display, bacterial display or mammalian display.

In other embodiments the POI library is fused to the capture protein and the anchor protein is fused to the tether sequence.

In yet other embodiments, the system described in the first embodiment uses a SpyTag/SpyCatcher system to spontaneously form a covalent bond and link the POI to the anchor protein. The SpyTag or a modified or optimized version of it, e.g., SpyTag002, is the tether sequence and the SpyCatcher or a modified or optimized version of it, e.g., SpyCatcher002, is the capture sequence. The POI is either fused to the SpyTag and the anchor protein is fused to the SpyCatcher or the POI is fused to the SpyCatcher and the SpyTag is fused to the anchor protein.

In other embodiments, the system described in the first embodiment uses a different protein ligation system than the SpyTag/SpyCatcher to link the POI to the anchor protein such as the SnoopTag/SnoopCatcher (Veggiani et al., 2016), SpyTag/KTag/SpyLigase (Fierer et al., 2014), Sortase system (Schmohl et al., 2014), split inteins (Thiel et al., 2014), Butelase 1 (Nguyen et al., 2014), Peptiligase (Toplak et al., 2016), or other similar methods.

In a yet another embodiment, a POI, such as an antibody fragment or single chain antibody library with a tethering sequence at the C-terminus of the heavy or light chain and one or more additional tags which can be used for antibody purification or detection is expressed. A filamentous phage, such as M13, is the biological entity. Production of phage with the POI displayed on the surface of the phage is achieved by infection of bacteria carrying a phagemid with the POI-tethering sequence fusion gene with a modified helper phage. The modified helper phage produces a capture sequence-pIII fusion instead of wildtype pIII. The modified pIII might contain a protease cleavage site between the capture sequence and pIII, such as TEV, rhinovirus 3C protease or trypsin, for elution of selected phage by protease cleavage. Furthermore, bacteria carrying a plasmid which encodes a capture sequence-pIII fusion protein or modified bacteria which carry a capture sequence-pIII gene in their genome can be used in combination with helper phage infection to produce new POI displaying phage. Instead of a complete pIII fusion, an optimized, modified or truncated pIII fusion might be used.

In another embodiment, a POI, such as an antibody fragment or single chain antibody library with a capture sequence at the C-terminus of the heavy or light chain and one or more additional tags which can be used for antibody purification or detection is expressed. A filamentous phage, such as M13, is the biological entity. Production of phage with the POI displayed on the surface of the phage is achieved by infection of bacteria carrying a phagemid with the POI-capture sequence fusion gene with a modified helper phage. The modified helper phage produces a tethering sequence-pIII fusion instead of wildtype pIII. The modified pIII might contain a protease cleavage site between the tethering sequence and pIII, such as TEV, rhinovirus 3C protease or trypsin, for elution of selected phage by protease cleavage. Furthermore, bacteria carrying a plasmid which encodes a tethering sequence-pIII fusion protein or modified bacteria which carry a tethering sequence-pIII gene in their genome can be used in combination with helper phage infection to produce new POI displaying phage. Instead of a complete pIII fusion, an optimized, modified or truncated pIII fusion might be used.

As used in this specification and claims, the singular form "a," "an," and "the" include plural references unless the context clearly dictates otherwise.

As used herein the term "genetic constructs" refers to polynucleotide sequences encoding a protein of interest (POI) that is fused, in frame, to a "tether sequence" (TS) or to a capture sequence (CS) or to a protein (also referred to as an "anchor protein") expressed on the surface or linked to the surface of a prokaryotic cell, eukaryotic cell, prokaryotic virus or phage, or eukaryotic virus that is fused, in frame, to a capture sequence or tether sequence. For ease of reference, GC1 refers to genetic constructs comprising POI fused to a tether sequence or capture sequence and GC2 refers to genetic constructs comprising a capture sequence or tether sequence fused to an anchor protein.

The terms "tether sequence" or "tethering sequence" relate to a sequence that is attached to a POI or anchor protein and that facilitates the formation of a covalent linkage to a capture moiety expressed either on the surface of a biological entity or fused to the POI. Non-limiting examples of tethering sequences include SpyTag sequences, including SpyTag002, SnoopTag sequences, Sortase motifs, a C-peptide, butelase substrates, and peptiligase substrates. The tether sequence may be fused to POI or anchor protein at the N- or C-terminus of such proteins or polypeptides or in an internal loop. Particularly, a spacer sequence (e.g., a glycine/serine rich spacer) may flank the tether sequence in order to enhance accessibility for reaction. The spacer may further include a site for specific proteolysis (e.g., by Factor X, thrombin, enterokinase, tobacco etch virus (TEV) NIa protease, rhinovirus 3C protease or trypsin), allowing specific release from a tether sequence.

The term "capture sequence" refers to a polypeptide fused to an anchor protein or POI with which a tethering sequence forms a covalent peptide linkage, for example SpyCatcher for the SpyTag tethering sequence. The capture sequence may be fused to the anchor protein or POI at the N- or C-terminus of such proteins or polypeptides or in an internal loop. Particularly, a spacer sequence (e.g., a glycine/serine rich spacer) may flank the capture sequence in order to enhance accessibility for reaction. The spacer may further include a site for specific proteolysis (e.g., by Factor X, thrombin, enterokinase, tobacco etch virus NIa protease, rhinovirus 3C protease or trypsin), allowing specific release from a capture sequence.

The term "prokaryotic system" refers to prokaryotic cells such as bacterial cells or prokaryotic viruses, prokaryotic phages or bacterial spores. The term "eukaryotic system" refers to eukaryotic cells including cells of animal, plants, fungi and protists, and eukaryotic viruses such as retrovirus, adenovirus, baculovirus. Prokaryotic and eukaryotic systems may be, collectively, referred to as "expression systems".

The term "expression cassette" is used here to refer to a functional unit that is built in a vector for the purpose of expressing recombinant proteins/peptides. An expression cassette includes a promoter or promoters, a transcription terminator sequence, a ribosome binding site or ribosome binding sites, and the cDNA encoding a tether sequence or a capture sequence. Other genetic components can be added to an expression cassette, depending on the expression system (e.g., enhancers and polyadenylation signals for eukaryotic expression systems).

As used herein the term "vector" refers to a nucleic acid molecule, preferably self-replicating, which transfers an inserted nucleic acid molecule into and/or between host cells. Typically vectors are circular DNA comprising a replication origin, a selection marker, and/or viral package signal, and other regulatory elements. Vector, vector DNA, plasmid DNA, phagmid DNA are interchangeable terms in description of this invention. The term includes vectors that function primarily for insertion of DNA or RNA into a cell, replication vectors that function primarily for the replication of DNA or RNA, and expression vectors that function for transcription and/or translation of the DNA or RNA. Also included are vectors that provide more than one of the above functions.

As used herein the term "expression vector" is a polynucleotide which, when introduced into an appropriate host cell, can be transcribed and translated into a polypeptide(s). The term "expression vector," refers to vectors that direct the soluble expression of proteins of interest fused in frame with a tether sequence which is characterized by an ability to form a peptide linkage to capture sequence with a capture sequence produced by a helper vector as disclosed herein. The POI may also be fused in frame with a capture sequence which is characterized by an ability to form a peptide linkage to tether sequence with a tether sequence produced by a helper vector as disclosed herein.

The term "helper vector" refers to a genetic system, or host cell-specific vector designed to produce fusion proteins comprising an anchor protein fused in frame with a capture sequence. The anchor protein may also be fused in frame with a tether sequence. Helper vectors can be introduced into expression systems, in combination with an expression vector, transiently by co-transformation, permanently by integration into host genome, or by viral or phage infection of the host cells.

As used herein the term "display vector set" refers to particular combinations of expression vectors (which provide GC1 constructs) and helper vectors (which provide GC2 constructs). The co-expression of the GC1 and GC2 result in the display of POI on the surface of an expression system.

The term "anchor protein" as used herein, refers to a polypeptide or protein of which a portion is found outside the cell membrane or the outer surface of an expression system. Capture sequences or tether sequences are fused to the portion of the anchor protein, (usually the N-terminal portion of the anchor protein) that is found on the outer surface of a cell (see, for example, FIG. 1). Non-limiting examples of anchor proteins are provided in Table 1 or have been disclosed in other publications, such as Little et al., which is hereby incorporated by reference in its entirety.

Where phage display systems, such as bacteriophage M13 virus particles are used as an expression system, captures sequences or tether sequences can be fused, in frame, to coat proteins, such as within genes III, VI, VII, VIII and IX, modified or truncated coat proteins such as long, short or supershort versions of pIII. Alternatively, capture sequences or tether sequences can be expressed on the surface of bacterial cells, such as *E. coli*. For example, capture sequences can be fused to anchor proteins such as outer membrane proteins (Chang and Lo, 2000; Lee et al., 2004, pili and flagella (Westerlund-Wikstrom et al., 1997), modified lipoproteins (Georgiou et al., 1996), ice nucleation proteins (Jung et al., 1998), or autotransporters (Veiga et al., 2003).

Capture sequences can also be displayed on the surfaces of eukaryotic host cells, such as *Saccharomyces cerevisiae*. For example, the cell wall protein alpha-agglutinin 1 and alpha-agglutinin 2, Cwp1, Cwp2, Gas1p, Yap3p, Flo1p, Crh2p, Pir1, Pir2, Pir4, and Icwp in *S. cerevisiae*; HpSEDI, HpGASI, HpTIPI, HPWPI in *Hansenula polymorpha*, and Hwp1p, Als3p, Rbt5p in *Candida albicans* can be used to display capture sequences on yeast cell surfaces.

Likewise, mammalian cells can be manipulated to express capture sequences on the cell surface. For example, a capture sequence can be expressed on membrane anchor proteins, such as cell surface receptors (Chesnut et al., 1996, J Immunological Methods; Ho et al, 2006, PNAS, 103:9637-9642), GPI anchor sequences (U.S. Pat. No. 6,838,446), non-cleavable type 11 signal anchor sequences (U.S. Pat. No. 7,125,973).

TABLE 1

Examples for different surface display systems

| Display System | Anchor | Anchor | References |
|---|---|---|---|
| Phage | pIII | M13 Coat Protein | McCafferty et al. (1990) |
| | | | Bastien et al. (1997) |
| | pVIII | M13 Coat Protein | Benhar (2001) |
| | pVII and pIX | | Gao et al. (1999) |
| | | | Tornetta et al. (2012) |
| Virus-like particles | VP1 | Polyoma virus coat | Gleiter and Lilie (2001) |
| | L1 | Human papilloma virus | Koutsky et al. (2002) |
| Gram-negative cells | LamB | Maltoporin | Benhar (2001) |
| | OmpA | Outer membrane protein | Benhar (2001) |
| | Lpp-OmpA | Lipoprotein/OmpA chimere | Chen and Georgiou (2002) |
| | INP | Ice nucleation protein | Li et al. (2003) |
| | FliC | Flagellae protein (flagellin) | Lu et al. (1995) |
| | FimA | Fimbriae protein (fimbrillin) | Samuelson et al. (2002) |
| Gram-positive Cells | Protein A | Cell wall anchor (covalent) | Steidler et al. (1998) |
| | LysM | Cell wall anchor (non-covalent) | Shao et al. (2009) |
| | FnBPB | Fibronectin-binding protein | Strauss and Götz (1996) |
| | M6 | Cell wall binding | Wieczorek and Martin (2010) |
| S-layers | SbpA | *Lysinibacillus sphaericus* | Ilk et al. (2011) |
| | RsaA | *Caulobacter crescentus* | Nomellini et al. (2007) |
| Yeast | Agα1 | α-agglutinin | Shimojo et al. (2004) |
| | Aga1/Aga2 | a-agglutinin | Borodina et al. (2010) |
| | | | Wen et al. (2010) |
| | Flo1 | Flocculin | Matsumoto et al. (2002) |
| Endo-spores | CotB, C, D | Coat proteins | Isticato et al. (2001) |
| | | | Mauriello et al. (2004) |
| | | | Duc et al. (2007) |

As used herein the terms "polynucleotides", "nucleic acids", "nucleotides" and "oligonucleotides" are used interchangeably. They refer to a polymeric form of nucleotides of any length, either deoxyribonucleotides or ribonucleotides, or analogs thereof. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the nucleotide polymer.

As used herein the term "amino acid" refers to either natural and/or unnatural or synthetic amino acids, including glycine and both the D or L optical isomers, and amino acid analogs and peptidomimetics.

As used herein the terms "polypeptide", "peptide", and "protein," are used interchangeably herein to refer to polymers of amino acids of any length. POI may, thus, be a polypeptide, peptide or protein.

A "protein of interest" (POI) is any desired polypeptide, peptide, or protein. Non-limiting examples of POI include antibodies, for example full length antibodies, antibody fragments, single chain antibodies (e.g., scFv, scFab, or single domain antibodies, protein scaffolds (e.g. based on fibronectin III, cystatin, lipocalins, Ankyrin repeat domains, Z domain of protein A and others), hormones, interleukins, antigens for the development of vaccines, enzymes, etc. Other examples include, and are not limited to: human growth hormone (hGH), N-methionyl human growth hormone, bovine growth hormone, parathyroid hormone, thyroxine, insulin A-chain, insulin B-chain, proinsulin, relaxin A-chain, relaxin B-chain, prorelaxin, glycoprotein hormones such as follicle stimulating hormones (FSH), thyroid stimulating hormone (TSH), and leutinizing hormone (LH), glycoprotein hormone receptors, calcitonin, glucagon, factor VIII, an antibody, lung surfactant, urokinase, streptokinase, human tissue-type plasminogen activator (t-PA), bombesin, factor IX, thrombin, hemopoietic growth factor, tumor necrosis factor-alpha and -beta, enkephalinase, human serum albumin, mullerian-inhibiting substance, mouse gonadotropin-associated peptide, a microbial protein, such as betalactamase, tissue factor protein, inhibin, activin, vascular endothelial growth factor, receptors for hormones or growth factors; integrin, thrombopoietin, protein A or D, rheumatoid factors, nerve growth factors such as NGF-β, platelet-growth factor, transforming growth factors (TGF) such as TGF-alpha and TGF-beta, insulin-like growth factor-I and -II, insulin-like growth factor binding proteins, CD-4, DNase, latency associated peptide, erythropoietin, osteoinductive factors, interferons such as interferon-alpha, -beta, and -gamma, colony stimulating factors (CSFs) such as M-CSF, GF-CSF, and G-CSF, interleukins (ILs) such as IL-1, IL-2, IL-3, IL-4, superoxide dismutase; decay accelerating factor, viral antigen, HIV envelope proteins such as GP120, GP140, atrial natriuretic peptides A, B or C, immunoglobulins, and fragments of any of the above-listed proteins.

As used herein the term "host cell" includes an individual cell or cell culture which can be, or has been, a recipient for the disclosed vectors. Host cells include progeny of a single host cell. The progeny may not necessarily be completely identical to the original parent cell due to natural, accidental, or deliberate mutation.

As used herein, a polypeptide or polynucleotide sequence is "essentially identical" or "substantially similar" to comparison sequence, if both sequences exhibit substantial amino acid or nucleotide sequence homology. Generally, essentially identical or substantially identical sequences are at least about 60% identical with each other, after alignment to the homologous regions. Preferably, the sequences are at least about 70% identical, more preferably, they are at least about 80% identical, more preferably, they are at least about 90% identical, of more preferably, the sequences are at least about 95% identical.

Tether and Capture Sequences

Tether and capture sequences are protein or peptide sequences which can form a covalent bond to each other spontaneously or enzymatically with or without addition or involvement of other factors (proteins, enzymes, catalysts, salts etc.). A few non-limiting examples are listed below.

SpyTag/SpyCatcher

U.S. Pat. No. 9,547,003 (the disclosure of which is hereby incorporated by reference in its entirety) discloses the components of the SpyTag/SpyCatcher system (used as a tether).

As discussed therein, in this respect, the tether sequence about 5-50 amino acids in length (e.g., about 10, 20, 30, 40 or 50 amino acids in length) and is derived from SEQ ID NOs: 1, 3, 5 or 6. Capture sequences are also derived from SEQ ID NOs: 1, 3, 5 or 6 and can be of any length.

The tether sequence and capture sequence may be fused to POI at the N- or C-terminus of such proteins or polypeptides or in an internal loop. Particularly, a spacer sequence (e.g., a glycine/serine rich spacer) may flank the tether sequence or the capture sequence in order to enhance accessibility for reaction. The spacer may further include a site for specific proteolysis (e.g., by Factor X, thrombin, enterokinase or tobacco etch virus NIa protease), allowing specific release from a tether or capture sequence. Thus, the tether sequence comprises residues 302-308 of the sequence set out in SEQ ID NO: 1, SEQ ID NO: 25 (mgsshhhhhh ssglvprgsv ptivmvdayk rykgsgesgk), SEQ ID NO: 27 (VP-TIVMVDAYKRYKS), or a sequence with at least 50% identity to SEQ ID NO: 1, 25 or 27, wherein said peptide tag is less than 50 amino acids in length. In certain embodiments, the tether sequence has at least about 55%, about 60%, about 65%, about 70%, about 75%, about 80%, about 85%, about 90%, or about 95% identity to SEQ ID NO: 1 and is less than 50 amino acids in length. More particularly, the tether sequence may comprise residues 301-308, 300-308, 299-308, 298-308, 297-308, 296-308, 295-308, 294-308, 293-308, 292-308, 291-308 or 290-308 of SEQ ID NO: 1 or a sequence with at least about 50% to 95% identity to residues 302-308 of SEQ ID NO: 1 or 25. Preferably the tether sequence comprises the reactive asparagine of position 303 in SEQ ID NO: 1, i.e., this residue is preferably unchanged. Further, the tether sequence may be a fragment of SEQ ID NO: 1 or 25 and, in a preferred embodiment, a tether sequence of less than 50 amino acids and which comprises residues 293-308 of the sequence set forth in SEQ ID NO: 1 or which comprises a sequence with at least 50% identity thereto is used. The peptide tags are length restricted and comprise less than 50 amino acid residues. Thus the peptide tags do not comprise the sequence of SEQ ID NO: 1 but only specific fragments thereof, or sequences with at least 50% identity e.g., 75, 80, 85, 90 or 95% identity to such specific fragments. Other embodiments utilize SEQ ID NO: 25 or a sequence having at least 50% sequence identity thereto as a tether sequence.

The capture sequence comprises or consists of residues 31-291 of the sequence set out in SEQ ID NO: 1, SEQ ID NO: 26 (msyyhhhhhh dydipttenl yfqgamvttl sglsgeqgps gdmtteedsa thikfskrde dgrelagatm elrdssgkti stwisdghvk dfylypgkyt fvetaapdgy evataitftv neqgqvtvng eatkgdaht), SEQ ID NO: 28 (yfqgamvttl sglsgeqgps gdmtteedsa thikfskrde dgrelagatm elrdssgkti stwisdghvk dfylypgkyt fvetaapdgy evataitftv neqgqvtvng eatkgdaht) or a sequence with at least 50% identity thereto e.g., with 75, 80, 85, 90, 95, 96, 97, 98 or 99% identity to residues 32-291 of SEQ ID NO: 1 or SEQ ID NO: 26 or SEQ ID NO: 28 (yfqgamvttl sglsgeqgps gdmtteedsa thikfskrde dgrelagatm elrdssgkti stwisdghvk dfylypgkyt fvetaapdgy evataitftv neqgqvtvng eatkgdaht). Specifically excluded is the complete sequence set out in SEQ ID NO: 1, however, the capture sequence should contain the reactive lysine corresponding to position 179 of SEQ ID NO: 1. Particularly, the binding partner comprises residues 31-292, 31-293, 31-294, 31-295, 31-296, 31-297, 31-298, 31-299, 31-300, 31-301 or 31-302 of the sequence set forth in SEQ ID NO: 1 or a sequence with at least 70% identity thereto, excluding the sequence of SEQ ID NO: 1.

Additionally, a tether sequence may be designed from the major pilin protein Spy0128 using the alternative isopeptide bond in the N-terminus. Therefore, tether sequence may be designed or is obtainable from an N-terminal fragment of the isopeptide protein and the remaining, truncated or overlapping protein fragment may constitute the capture sequence. The reactive lysine involved in the isopeptide bond at the N-terminus is found at position 36 of SEQ ID NO: 1 and the reactive asparagine involved in the isopeptide bond is found at position 168 of SEQ ID NO: 1. Thus, in a preferred embodiment the tether sequence comprises the reactive lysine residue in this instance and the capture sequence comprises the reactive asparagine. Particularly, a tether sequence comprises residues 31-40 of the sequence set out in SEQ ID NO: 1 or a sequence with at least 70% identity thereto and is less than 50 amino acids in length. The corresponding capture sequence for the above described tether sequence comprises residues 37-304 of the sequence set out in SEQ ID NO: 1 or has a sequence with at least 70% identity thereto, excluding the sequence of SEQ ID NO: 1. Preferably, the reactive residues in the peptide tag and binding partner are not mutated.

Another tether sequence comprises residues 179-184 e.g., 173-185 of the sequence set out in SEQ ID NO: 3 or has a sequence with at least 50% identity thereto and is less than 50 amino acids in length. The capture sequence comprises residues 191-317 e.g., 186-318 of SEQ ID NO: 3 or a sequence having at least 50% identity thereto, excluding SEQ ID NO: 3. Specifically excluded as a tether sequence or a capture sequence is the full length sequence of SEQ ID NO: 3.

Another tether sequence comprises fragments of SEQ ID NO: 5 that include the asparagine at position 266 (or sequences having at least 50% identity thereto) and a capture sequence comprising fragments of SEQ ID NO: 5 that have at least 50% sequence identity thereto and which comprises the lysine residue at position 149 but which does not include the asparagine at position 266. Neither the tether sequence nor the capture sequence comprise SEQ ID NO: 5.

In another embodiment, the tether sequence comprises a fragment of SEQ ID NO: 6 that includes the aspartic acid residue at position 101 (or a sequence at least 70% identical thereto) and the capture sequence comprises fragments of SEQ ID NO: 6 that contain the reactive lysine of position 15 (or sequences at least 50% identical thereto). Neither the tether sequence nor the capture sequence comprise SEQ ID NO: 6.

Another embodiment provides for a tether sequence comprising SEQ ID NO: 25 (mgsshhhhhh ssglvprgsv ptivmvdayk rykgsgesgk), SEQ ID NO: 27 (VPTIVMVDAYKRYKS), or a sequence with at least 50% identity to SEQ ID NO: 25 or 27, wherein said peptide tag is 15 to 40 or 50 amino acids in length. In certain embodiments, the tether sequence has at least about 55%, about 60%, about 65%, about 70%, about 75%, about 80%, about 85%, about 90%, or about 95% identity to SEQ ID NO: 25 or 27 and is less than 50 amino acids in length. Preferably the tether sequence comprises the reactive aspartic acid of position 8 in SEQ ID NO: 27, i.e., this residue is preferably unchanged.

A capture sequence for either of SEQ ID NO: 25, 27 or a sequence with at least 50% identity to SEQ ID NO: 25 or 27, that is 15 to 40 or 50 amino acids in length and contains an aspartic acid of position 8 in SEQ ID NO: 27, comprises or consists of SEQ ID NO: 26 (msyyhhhhhh dydipttenl yfqgamvttl sglsgeqgps gdmtteedsa thikfskrde dgrelagatm elrdssgkti stwisdghvk dfylypgkyt fvetaapdgy evataitftv neqgqvtvng eatkgdaht) or yfqgamvttl sglsgeqgps gdmtteedsa thikfskrde dgrelagatm elrdssgkti stwisdghvk dfylypgkyt fvetaapdgy evataitftv neqgqvtvng eatkgdaht, or a sequence with at least 50% identity thereto e.g., with 75, 80, 85, 90, 95, 96, 97, 98 or 99% identity to SEQ ID NO: 26 or SEQ ID NO: 28 (yfqgamvttl sglsgeqgps gdmtteedsa thikfskrde dgrelagatm elrdssgkti stwisdghvk dfylypgkyt fvetaapdgy evataitftv neqgqvtvng eatkgdaht). Variants have at least 50% sequence identity and retain the lysine at position 57 of SEQ ID NO: 26.

SpyLigase/SnoopLigase

Alternatively, POI can be attached to exposed surface proteins using the systems described in WO2016/193746 (which is hereby incorporated by reference in its entirety). In such embodiments, tether sequences are attached to both the POI and an anchor protein, optionally through linker sequences, such as a glycine/serine rich spacer. These tether sequences are then ligated by a ligase that is also encoded by the host cell. The tether sequence can, in some embodiments, have a length between 6-50 amino acids, e.g., 7-45, 8-40, 9-35, 10-30, 11-25 amino acids in length, e.g. it may comprise or consist of 6, 7, 8, 9, 10, 11, 12, 13, 14, 15, 16, 17, 18, 19 or 20 amino acids. Other embodiments provide a tether sequence of about 20-300 amino acids in length (e.g., about 10, 20, 30, 40, 50, 60, 70, etc. amino acids length). In some embodiments, the peptide ligase may be between 50-300 amino acids in length, e.g., 60-250, 70-225, 80-200 amino acids in length, e.g., it may comprise or consist of 60, 65, 70, 75, 80, 85, 90, 95, 100, 110, 120, 130, 140, 150, 160, 170, 180, 190 or 200 amino acids, providing it meets the definitions set forth for the ligase, below. Tether sequences attached to an anchor protein correspond to a capture sequence in this aspect of the invention.

A pair of tether sequences may be derived from any suitable isopeptide protein. For instance, tether sequences may be derived from the major pilin protein Spy0128, which has an amino acid sequence as set out in SEQ ID NO: 7 and is encoded by a nucleotide sequence as set out in SEQ ID NO: 8. Two isopeptide bonds are formed in the protein. One isopeptide bond is formed between lysine at position 179 in SEQ ID NO: 7 and asparagine at position 303 in SEQ ID NO: 7 (the reactive residues). The glutamic acid residue which induces the spontaneous isopeptide bond is found at position 258 in SEQ ID NO: 7. Thus, a pair of tether sequences developed from an isopeptide protein set forth in SEQ ID NO: 7 will preferably comprise a tether sequence comprising a fragment of the protein comprising the reactive asparagine at position 303 and a tether sequence comprising a fragment of the protein comprising the reactive lysine at position 179. A fragment of the protein comprising the glutamic acid residue at position 258 can be provided separately, i.e., as a peptide ligase that forms the isopeptide bond.

Another isopeptide bond in the major pilin protein Spy0128 occurs between the lysine residue at position 36 of SEQ ID NO: 7 and the asparagine residue at position 168 of SEQ ID NO: 7. The glutamic acid residue which induces isopeptide formation is found at position 117 in SEQ ID NO: 7. Thus, a pair of tether sequences developed from an isopeptide protein set forth in SEQ ID NO: 7 will preferably comprise a tether sequence comprising a fragment of the protein comprising the reactive lysine residue at position 36 and a tether sequence comprising a fragment of the protein comprising the reactive asparagine at position 168. A fragment of the protein comprising the glutamic acid residue at position 117 may be provided separately as a peptide ligase.

An isopeptide bond occurs between a lysine residue at position 181 of SEQ ID NO: 9 (ACE19, a domain of an adhesin protein from *E. faecalis*) and an asparagine residue at position 294 of SEQ ID NO: 9. The bond is induced by an aspartic acid residue at position 213 in SEQ ID NO: 9. Thus, a pair of tether sequences developed from isopeptide protein set forth in SEQ ID NO: 9 will preferably comprise a tether sequence comprising a fragment of the protein comprising the reactive asparagine residue at position 294 and a tether sequence comprising a fragment of the protein comprising the reactive lysine residue at position 181. A fragment of the protein comprising the aspartic acid residue at position 213 may be provided separately as a peptide ligase.

The collagen binding domain from *S. aureus* which has an amino acid sequence set out in SEQ ID NO: 10 can also be used. The isopeptide bond occurs between lysine at position 176 of SEQ ID NO: 10 and asparagine at position 308 of SEQ ID NO: 10. The aspartic acid residue which induces the isopeptide bond is at position 209 of SEQ ID NO: 10. Thus, a pair of tether sequences developed from the isopeptide protein set forth in SEQ ID NO: 10 will preferably comprise a tether sequence comprising a fragment of the protein comprising the reactive lysine at position 176 and a tether sequence comprising a fragment of the protein comprising the reactive asparagine at position 308. A fragment of the protein comprising the aspartic acid residue at position 209 may be provided separately as a peptide ligase.

FbaB from *Streptococcus pyogenes* can also be used to provide tether sequences and comprises a domain, CnaB2, which has an amino acid sequence set out in SEQ ID NO: 11, is encoded by the nucleotide sequence set out in SEQ ID NO: 12. The isopeptide bond in the CnaB2 domain forms between a lysine at position 15 of SEQ ID NO: 11 and an aspartic acid residue at position 101 of SEQ ID NO: 11. The glutamic acid residue which induces the isopeptide bond is at position 61 of SEQ ID NO: 11. Thus, a pair of tether sequences developed from the isopeptide protein set forth in SEQ ID NO: 11 will preferably comprise a tether sequence comprising a fragment of the protein comprising the reactive lysine at position 15 and a tether sequence comprising a fragment of the protein comprising the reactive aspartic acid at position 101. A fragment of the protein comprising the glutamic acid residue at position 61 may be provided separately as a peptide ligase.

The RrgA protein is an adhesion protein from *Streptococcus pneumoniae*, which has an amino acid sequence as set out in SEQ ID NO: 13 and is encoded by a nucleotide sequence as set out in SEQ ID NO: 14. An isopeptide bond is formed between lysine at position 742 in SEQ ID NO: 13 and asparagine at position 854 in SEQ ID NO: 13. The bond is induced by a glutamic acid residue at position 803 in SEQ ID NO: 13. Thus, a pair of tether sequences developed from the isopeptide protein set forth in SEQ ID NO: 13 will preferably comprise a tether sequence comprising a fragment of the protein comprising the reactive asparagine at position 854 and a tether sequence comprising a fragment of the protein comprising the reactive lysine at position 742. A fragment of the protein comprising the glutamic acid residue at position 803 may be provided separately as a peptide ligase as defined above.

The PsCs protein is a fragment of the por secretion system C-terminal sorting domain protein from *Streptococcus intermedius*, which has an amino acid sequence as set out in SEQ ID NO: 15 and is encoded by a nucleotide sequence as set out in SEQ ID NO: 16. An isopeptide bond is formed between lysine at position 405 in SEQ ID NO: 15 and aspartate at position 496 in SEQ ID NO: 15. Thus, a pair of tether sequences developed from the isopeptide protein set forth in SEQ ID NO: 15 will preferably comprise a tether sequence comprising a fragment of the protein comprising the reactive aspartate at position 496 and a tether sequence comprising a fragment of the protein comprising the reactive lysine at position 405.

In various embodiments, tether sequences may be derived from an isopeptide protein comprising an amino acid sequence as set forth in any one of SEQ ID NO: 21, 23, 25 or 27 or a protein with at least 70% sequence identity to an amino acid sequence as set forth in any one of SEQ ID NO: 21, 23, 25 or 27. In some embodiments, said isopeptide protein sequence above is at least 75, 80, 85, 90, 95, 96, 97, 98, 99 or 100% identical to the sequence (SEQ ID NO: 21, 23, 25 or 27) to which it is compared.

Sortase

Another means for tethering POI to anchor proteins comprises the use of sortase enzymes and sortase recognition and bridging domains. Schmohl et al. (2014), which is hereby incorporated by reference in its entirety, discuss sortase mediated ligation for the site-specific modification of proteins. In this aspect of the invention, the sortase recognition and bridging domains are considered tethering sequences and the tethering sequence fused to an anchor protein corresponds to a capture sequence in this aspect of the invention. Sortases are transpeptidases produced by Gram-positive bacteria to anchor cell surface proteins covalently to the cell wall. The *Staphylococcus aureus* sortase A (SrtA) cleaves a short C-terminal recognition motif (LPXTG (SEQ ID NO: 17) (referred to herein as a sortase recognition domain). The sortase recognition domain is a sortase A recognition domain or a sortase B recognition domain. In particular embodiments, the sortase recognition domain comprises or consists of the amino acid sequence: LPTGAA (SEQ ID NO: 18), LPTGGG (SEQ ID NO: 19), LPKTGG (SEQ ID NO: 20), LPETG (SEQ ID NO: 21), LPXTG (SEQ ID NO: 22) or LPXTG(X)$_n$ (SEQ ID NO: 23), where X is any amino acid, and n is 0, 1, 2, 3, 4, 5, 7, 8, 9, 10, in the range of 0-5 or 0-10, or any integer up to 100. The sortase recognition domain can be fused, in frame, to a POI or an anchor protein, optionally through a glycine/serine rich spacer. Where it is attached to a POI, it is considered a tether sequence and where it is attached to an anchor protein, it is considered a capture sequence.

The sortase A bridging domain comprises one or more glycine residues at one of its termini. In certain embodiments, the one or more glycine residues may optionally be: Gly, (Gly)$_2$, (Gly)$_3$, (Gly)$_4$, or (Gly)$_x$, where x is an integer of 1-20. The sortase bridging domain can be attached to a POI or an anchor protein, optionally through a glycine/serine rich spacer. Where it is attached to a POI, it is considered a tether sequence and where it is attached to an anchor protein, it is considered a capture sequence.

The sortase B recognition domain comprises the amino acid sequence NPX1TX2 (SEQ ID NO: 31), where X1 is glutamine or lysine; X2 is asparagine or glycine; N is asparagine; P is proline and T is threonine. The sortase B. The sortase recognition domain can be fused, in frame, to a POI or an anchor protein, optionally through a glycine/serine rich spacer. Where it is attached to a POI, it is considered a tether sequence and where it is attached to an anchor protein, it is considered a capture sequence.

The sortase B bridging domain comprises one or more glycine residues at one of its termini. In certain embodiments, the one or more glycine residues may optionally be: Gly, (Gly)$_2$, (Gly)$_3$, (Gly)$_4$ (SEQ ID NO: 32), or (Gly)$_x$, where x is an integer of 1-20. The sortase bridging domain can be attached to a POI or an anchor protein, optionally through a glycine/serine rich spacer. Where it is attached to a POI, it is considered a tether sequence and where it is attached to an anchor protein, it is considered a capture sequence.

Butelase 1

Yet another means for tethering a POI to an anchor protein comprises the use of butelase 1 to form a peptide bond between the butelase recognition motif (where Asx is Asn or Asp) and the amino terminus of another polypeptide. In this case, the Asx-His-Val motif can be fused, in frame, to a POI or an anchor protein, optionally through a glycine/serine rich spacer. Butelase can then be used to form a peptide bond between the Asx-His-Val motif and the N-terminal amino acid of the anchor protein. WO 2017/058114, which is hereby incorporated by reference in its entirety, discloses methods and materials for butelase-mediated peptide ligation.

Split Inteins

Another method for tethering a POI to an anchor protein comprises the use of split inteins. Inteins can exist as two fragments encoded by two separately transcribed and translated genes. These so-called split inteins self-associate and catalyze protein-splicing activity in trans. Split inteins have been identified in diverse cyanobacteria and archaea (Caspi et al., 2003; Choi J. et al., 2006; Dassa B. et al., 2007; Liu X. and Yang J., 2003; Wu H. et al., 1998; and Zettler J. et al., 2009, the disclosures of which are hereby incorporated by reference in their entireties). Thiel et al. (2014) and WO 2013/045632, each of which is hereby also incorporated by reference in its entirety, also disclose the use of split inteins that can be used to fuse heterologous proteins.

Vectors

The vectors of the present invention generally comprise transcriptional or translational control sequences required for expressing the POI and anchor proteins. Suitable transcription or translational control sequences include but are not limited to replication origin, promoter, enhancer, repressor binding regions, transcription initiation sites, ribosome binding sites, translation initiation sites, and termination sites for transcription and translation.

The origin of replication (generally referred to as an ori sequence) permits replication of the vector in a suitable host cell. The choice of ori will depend on the type of host cells and/or genetic packages that are employed. Where the host cells are prokaryotes, the expression vector typically comprises two ori sequences, one directing autonomous replication of the vector within the prokaryotic cells, and the other ori supports packaging of the phage particles. Preferred prokaryotic ori is capable of directing vector replication in bacterial cells. Non-limiting examples of this class of ori include pMB1, pUC, as well as other *E. coli* origins. Preferred ori supporting packaging of the phage particles includes but is not limited to f1 ori, Pf3 phage replication ori.

In the eukaryotic system, higher eukaryotes contain multiple origins of DNA replication, but the ori sequences are not clearly defined. The suitable origins of replication for mammalian vectors are normally from eukaryotic viruses. Preferred eukaryotic ori include, but are not limited to, SV40 ori, EBV ori, or HSV ori.

As used herein, a "promoter" is a DNA region capable under certain conditions of binding RNA polymerase and initiating transcription of a coding region located downstream (in the 3' direction) from the promoter. It can be constitutive or inducible. In general, the promoter sequence is bounded at its 3' terminus by the transcription initiation site and extends upstream (5' direction) to include the minimum number of bases or elements necessary to initiate transcription at levels detectable above background. Within the promoter sequence is a transcription initiation site, as well as protein binding domains responsible for the binding of RNA polymerase. Eukaryotic promoters will often, but not always, contain "TATA" boxes and "CAT" boxes.

The choice of promoters will largely depend on the host cells in which the vector is introduced. For prokaryotic cells, a variety of robust promoters are known in the art. Preferred promoters are lac promoter, Trc promoter, T7 promoter and pBAD promoter. Normally, to obtain expression of exogenous sequence in multiple species, the prokaryotic promoter can be placed immediately after the eukaryotic promoter, or inside an intron sequence downstream of the eukaryotic promoter.

Suitable promoter sequences for eukaryotic cells include the promoters for 3-phosphoglycerate kinase, or other glycolytic enzymes, such as enolase, glyceraldehyde-3phosphate dehydrogenase, hexokinase, pyruvate decarboxylase, phosphofructokinase, glucose-6phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Preferred promoters for mammalian cells are SV40 promoter, CMV promoter, β-actin promoter and their hybrids. Preferred promoters for yeast cell includes but is not limited to GAL 10, GAL I, TEFI in *S. cerevisiae*, and GAP, AOX1 in *P. pastoris*.

In constructing the subject vectors, the termination sequences associated with the exogenous sequence are also inserted into the 3' end of the sequence desired to be transcribed to provide polyadenylation of the mRNA and/or transcriptional termination signal. The terminator sequence preferably contains one or more transcriptional termination sequences (such as polyadenylation sequences) and may also be lengthened by the inclusion of additional DNA sequence so as to further disrupt transcriptional read-through. Preferred terminator sequences (or termination sites) of the present invention have a gene that is followed by a transcription termination sequence, either its own termination sequence or a heterologous termination sequence. Examples of such termination sequences include stop codons coupled to various yeast transcriptional termination sequences or mammalian polyadenylation sequences that are known in the art and are widely available. Where the terminator comprises a gene, it can be advantageous to use a gene which encodes a detectable or selectable marker; thereby providing a means by which the presence and/or absence of the terminator sequence (and therefore the corresponding inactivation and/or activation of the transcription unit) can be detected and/or selected.

In addition to the above-described elements, the vectors may contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will survive and/or grow under selective conditions. Typical selection genes encode protein(s) that (a) confer resistance to antibiotics or other toxins, e.g., ampicillin, kanamycin, neomycin, zeocin, G418, methotrexate, etc.; (b) complement auxotrophic deficiencies; or (c) supply critical nutrients not available from complex media. The choice of the proper marker gene will depend on the host cell, and appropriate genes for different hosts are known in the art.

In one embodiment, the expression vector is a shuttle vector, capable of replicating in at least two unrelated host systems. In order to facilitate such replication, the vector generally contains at least two origins of replication, one effective in each host system. Typically, shuttle vectors are capable of replicating in a eukaryotic host system and a prokaryotic host system. This enables detection of protein expression in the eukaryotic host (the expression cell type) and amplification of the vector in the prokaryotic host (the amplification cell type). Preferably, one origin of replication is derived from SV40 or 2u and one is derived from pUC, although any suitable origin known in the art may be used provided it directs replication of the vector. Where the vector is a shuttle vector, the vector preferably contains at least two selectable markers, one for the expression cell type and one for the amplification cell type. Any selectable marker known in the art or those described herein may be used provided it functions in the expression system being utilized.

The vectors encompassed by the invention can be obtained using recombinant cloning methods and/or by chemical synthesis. A vast number of recombinant cloning techniques such as PCR, restriction endonuclease digestion and ligation are well known in the art, and need not be described in detail herein. One of skill in the art can also use the sequence data provided herein or that in the public or proprietary databases to obtain a desired vector by any synthetic means available in the art. Additionally, using well-known restriction and ligation techniques, appropriate sequences can be excised from various DNA sources and integrated in operative relationship with the exogenous sequences to be expressed in accordance with the present invention.

The application also provides the following non-limiting items:

1. A combination of vectors comprising:
   a) a first vector comprising a genetic construct (GC1) comprising polynucleotide encoding a protein of interest (POI) fused, in frame, to a tether sequence; and
   b) a second vector comprising a genetic construct (GC2) comprising polynucleotide encoding an anchor protein fused, in frame, to a capture sequence, the tether sequence and capture sequence forming a covalent bond when brought into contact with one another either spontaneously or with the help of an enzyme or a combination of vectors comprising:
   a) a first vector comprising a genetic construct (GC1) comprising polynucleotide encoding a protein of interest (POI) fused, in frame, to a capture sequence; and
   b) a second vector comprising a genetic construct (GC2) comprising polynucleotide encoding an anchor protein fused, in frame, to a tether sequence, the tether sequence and capture sequence forming a covalent bond when brought into contact with one another either spontaneously or with the help of an enzyme;

2. The combination of vectors according to item 1, wherein each vector comprises transcriptional or translational control sequences for expressing the POI and anchor protein;

3. The combination of vectors according to item 1, wherein said transcription or translational control sequences are selected from replication origins, promoters, enhancers, repressor binding regions, transcription initiation sites, ribosome binding sites, translation initiation sites, and termination sites for transcription and translation;

4. The combination of vectors according to any one of items 1-3, wherein said POI is selected from antibodies, antibody fragments, single chain antibodies, scFv, scFab, single domain antibodies, protein scaffolds (e.g. based on fibronectin III, cystatin, lipocalins, Ankyrin repeat domains, Z domain of protein A and others), enzymes, hormones, interleukins, antigens for the development of vaccines, human growth hormone (hGH), N-methionyl human growth hormone, bovine growth hormone, parathyroid hormone, thyroxine, insulin A-chain, insulin B-chain, proinsulin, relaxin A-chain, relaxin B-chain, prorelaxin, follicle stimulating hormones (FSH), thyroid stimulating hormone (TSH), leutinizing hormone (LH), glycoprotein hormone receptors, calcitonin, glucagon, factor VIII, lung surfactant, urokinase, streptokinase, human tissue-type plasminogen activator (t-PA), bombesin, factor IX, thrombin, hemopoietic growth factor, tumor necrosis factor-alpha and -beta, enkephalinase, human serum albumin, mullerian-inhibiting substance, mouse gonadotropin-associated peptide, a microbial protein, beta-lactamase, tissue factor protein, inhibin, activin, vascular endothelial growth factor, receptors for hormones or growth factors; integrin, thrombopoietin, protein A or D, rheumatoid factors, nerve growth factors, NGF-β, platelet-growth factor, transforming growth factors (TGF), TGF-alpha, TGF-beta, insulin-like growth factor-I or -II, insulin-like growth factor binding proteins, DNase, latency associated peptide, erythropoietin, osteoinductive factors, interferons, interferon-alpha, interferon-beta, interferon-gamma, colony stimulating factors (CSFs), M-CSF, GF-CSF, and G-CSF, interleukins (ILs), IL-1, IL-2, IL-3, IL-4, superoxide dismutase; decay accelerating factor, viral antigens, HIV envelope proteins, GP120, GP140, and atrial natriuretic peptides A, B or C;

5. The combination of vectors according to any one of items 1-4, wherein said tethering sequence is selected from a SpyTag sequence selected from any one of SEQ ID NOs: 1, 3, 5, 6, 25 or 27 a protein with at least 50% sequence identity to an amino acid sequence as set forth in any one of SEQ ID NOs: 1, 3, 5, 6, 25 or 27, a SnoopTag sequence selected from any one of SEQ ID NOs: 13, 7, 11, 9, 10 or 15 or a protein with at least 70% sequence identity to an amino acid sequence as set forth in any one of SEQ ID NOs: 13, 7, 11, 9, 10 or 15, a sortase recognition domain or a sortase bridging domain, a butelase recognition motif or a split intein;

6. The combination of vectors according to any one of items 1-5, wherein capture sequence is a SpyCatcher sequence selected from any one of SEQ ID NOs: 1, 3, 5, 6, 26 or yfqgamvttlsglsgeqgpsgdmtteedsathikfskrdedgrelagat-melrdssgktistwisdghvkdfylypgkytfvetaapdg yevataitftv-neqgqvtvngeatkgdaht (SEQ ID NO: 28) a protein with at least 50% sequence identity to an amino acid sequence as set forth in any one of SEQ ID NOs: 1, 3, 5, 6, 26 or yfqgamvttlsglsgeqgpsgdmtteedsathikfskrdedgrelagat-melrdssgktistwisdghvkdfylypgkytfvetaapdg yevataitftv-neqgqvtvngeatkgdaht (SEQ ID NO: 28), a SnoopCatcher sequence selected from any one of SEQ ID NOs: 13, 7, 11, 9, 10 or 15 or a protein with at least 70% sequence identity to an amino acid sequence as set forth in any one of SEQ ID NOs: 13, 7, 11, 9, 10 or 15, a sortase recognition domain or a sortase bridging domain, a butelase recognition motif or a split intein;

7. The combination of vectors according to any one of items 1-6, wherein said anchor protein is selected from pIII, pVI, p VII, pVIII, pIX, outer membrane proteins of bacterial cells, pili, flagella modified bacterial lipoproteins, ice nucleation proteins, autotransporters, LamB, OmpA, Lpp-OmpA, INP, FliC, FimA, Protein A, LysM, FnBPB, M6, SbpA, RsaA, cell wall protein alpha-agglutinin 1, alpha-agglutinin 2, Cwp1, Cwp2, Gas1p, Yap3p, Flo1p, Crh2p, Pir1, Pir2, Pir4, Icwp, HpSEDI, HpGASI, HpTIPI, HPWPI, HwpIp, Als3p, Rbt5p, surface receptors, or GPI anchor sequences;

8. A prokaryotic or eukaryotic host cell comprising a combination of vectors according to any one of items 1-7;

9. The prokaryotic or eukaryotic host cell according to item 8, wherein and said host cell comprises a vector comprising a promoter operably linked to a polynucleotide encoding a ligase derived from SEQ ID NOs: 13, 7, 11, 9, 10 or 15 or a ligase having at least 70% sequence identity to a ligase derived from SEQ ID NOs: 13, 7, 11, 9, 10 or 15; a vector comprising a promoter operably linked to a comprising a polynucleotide encoding a sortase; or a vector comprising a promoter operably linked to a polynucleotide encoding a butelase; or said host cell comprises, incorporated into its genome, a promoter operably linked to: a polynucleotide encoding a ligase derived from SEQ ID NOs: 13, 7, 11, 9, 10 or 15 or a ligase having at least 70% sequence identity to a ligase derived from SEQ ID NOs: 13, 7, 11, 9, 10 or 15; a polynucleotide encoding a sortase; or a polynucleotide encoding a butelase;

10. A method for displaying a (poly)peptide/protein on the surface of a bacteriophage particle comprising: causing or allowing the attachment of a protein of interest (POI) to an anchor protein in the protein coat of said bacteriophage particle, wherein said attachment is caused by the formation of a peptide bond between a tether sequence fused to said POI and a capture sequence fused to said anchor protein;

11. The method according to item 10, wherein said tethering sequence is selected from a SpyTag sequence selected from any one of SEQ ID NOs: 1, 3, 5, 6, 25 or 27 or a protein with at least 50% sequence identity to an amino acid sequence as set forth in any one of SEQ ID NOs: 1, 3, 5, 6, 25 or 27, a SnoopTag sequence selected from any one of SEQ ID NOs: 13, 7, 11, 9, 10 or 15 or a protein with at least 70% sequence identity to an amino acid sequence as set forth in any one of SEQ ID NOs: 13, 7, 11, 9, 10 or 15, a sortase recognition domain or a sortase bridging domain, a butelase recognition motif or a split intein;

12. The method according to item 10, wherein capture sequence is a SpyCatcher sequence selected from any one of SEQ ID NOs: 1, 3, 5, 6, 26 or 28, a protein with at least 70% sequence identity to an amino acid sequence as set forth in any one of SEQ ID NOs: 1, 3, 5, 6, 26 or 28, a SnoopCatcher sequence selected from any one of SEQ ID NOs: 13, 7, 11, 9, 10 or 15 or a protein with at least 70% sequence identity to an amino acid sequence as set forth in any one of SEQ ID NOs: 13, 7, 11, 9, 10 or 15, a sortase recognition domain or a sortase bridging domain, a butelase recognition motif or a split intein;

13. The method according to any one of items 10-12, wherein said anchor protein is selected from pIII, pVI, pVII, pVIII, or pIX;

14. The method according to any one of items 10-13, wherein said POI is selected from antibodies, antibody fragments, single chain antibodies, scFv, scFab, single domain antibodies, protein scaffolds (e.g. based on fibronectin III, cystatin, lipocalins, Ankyrin repeat domains, Z domain of protein A and others), enzymes, hormones, interleukins, antigens for the development of vaccines, human growth hormone hGH), N-methionyl human growth hormone, bovine growth hormone, parathyroid hormone, thyroxine, insulin A-chain, insulin B-chain, proinsulin, relaxin A-chain, relaxin B-chain, prorelaxin, follicle stimulating hormones (FSH), thyroid stimulating hormone (TSH), leutinizing hormone (LH), glycoprotein hormone receptors, calcitonin, glucagon, factor VIII, lung surfactant, urokinase, streptokinase, human tissue-type plasminogen activator (t-PA), bombesin, factor IX, thrombin, hemopoietic growth factor, tumor necrosis factor-alpha and -beta, enkephalinase, human serum albumin, mullerian-inhibiting substance, mouse gonadotropin-associated peptide, a microbial protein, beta-lactamase, tissue factor protein, inhibin, activin, vascular endothelial growth factor, receptors for hormones or growth factors; integrin, thrombopoietin, protein A or D, rheumatoid factors, nerve growth factors, NGF-β, platelet-growth factor, transforming growth factors (TGF), TGF-alpha, TGF-beta, insulin-like growth factor-I or -II, insulin-like growth factor binding proteins, DNase, latency associated peptide, erythropoietin, osteoinductive factors, interferons, interferon-alpha, interferon-beta, interferon-gamma, colony stimulating factors (CSFs), M-CSF, GF-CSF, and G-CSF, interleukins (ILs), IL-1, IL-2, IL-3, IL-4, superoxide dismutase; decay accelerating factor, viral antigens, HIV envelope proteins, GP120, GP140, and atrial natriuretic peptides A, B or C;

15. The method according to item 14, wherein said POI is an antibody, antibody fragment, single chain antibody, scFv, scFab, or single domain antibody;

16. A method for displaying a (poly)peptide/protein on the surface of a prokaryotic or eukaryotic cell comprising: causing or allowing the attachment of a protein of interest (POI) to an anchor protein expressed on the outer surface of said prokaryotic or eukaryotic cell, wherein said attachment is caused by the formation of a peptide bond between a tether sequence fused to said POI and a capture sequence fused to said anchor protein;

17. The method according to item 16, wherein said tethering sequence is selected from a SpyTag sequence selected from any one of SEQ ID NOs: 1, 3, 5, 6, 25 or 27 a protein with at least 70% sequence identity to an amino acid sequence as set forth in any one of SEQ ID NOs: 1, 3, 5, 6, 25 or 27, a SnoopTag sequence selected from any one of SEQ ID NOs: 13, 7, 11, 9, 10 or 15 or a protein with at least 70% sequence identity to an amino acid sequence as set forth in any one of SEQ ID NOs: 13, 7, 11, 9, 10 or 15, a sortase recognition domain or a sortase bridging domain, a butelase recognition motif or a split intein;

18. The method according to item 16, wherein capture sequence is a SpyCatcher sequence selected from any one of SEQ ID NOs: 1, 3, 5, 6, 26, or 28 a protein with at least 70% sequence identity to an amino acid sequence as set forth in any one of SEQ ID NOs: 1, 3, 5, 6, 26, or 28, a Snoop-Catcher sequence selected from any one of SEQ ID NOs: 13, 7, 11, 9, 10 or 15 or a protein with at least 70% sequence identity to an amino acid sequence as set forth in any one of SEQ ID NOs: 13, 7, 11, 9, 10 or 15, a sortase recognition domain or a sortase bridging domain, a butelase recognition motif or a split intein;

19. The method according to any one of items 16-18, wherein said method comprises the expression of said POI on the surface of a prokaryotic cell and said anchor protein is selected from outer membrane proteins, pili, flagella, modified lipoproteins, ice nucleation proteins, autotransporters, LamB, OmpA, Lpp-OmpA, INP, FliC, FimA, Protein A, LysM, FnBPB, M6, SbpA, or RsaA;

20. The method according to any one of items 16-18, wherein said method comprises the expression of said POI on the surface of an eukaryotic cell and said anchor protein is selected from cell wall protein alpha-agglutinin 1, alpha-agglutinin 2, Cwp1, Cwp2, Gas1p, Yap3p, Flo1p, Crh2p, Pir1, Pir2, Pir4, Icwp, HpSEDI, HpGASI, HpTIPI, HPWPI, HwpIp, Als3p, Rbt5p, surface receptors, or GPI anchor sequences;

21. The method according to any one of items 16-19, wherein said POI is selected from antibodies, antibody fragments, single chain antibodies, scFv, scFab, single domain antibodies, protein scaffolds (e.g. based on fibronectin III, cystatin, lipocalins, Ankyrin repeat domains, Z domain of protein A and others), enzymes, hormones, interleukins, antigens for the development of vaccines, human growth hormone hGH), N-methionyl human growth hormone, bovine growth hormone, parathyroid hormone, thyroxine, insulin A-chain, insulin B-chain, proinsulin, relaxin A-chain, relaxin B-chain, prorelaxin, follicle stimulating hormones (FSH), thyroid stimulating hormone (TSH), leutinizing hormone (LH), glycoprotein hormone receptors, calcitonin, glucagon, factor VIII, lung surfactant, urokinase, streptokinase, human tissue-type plasminogen activator (t-PA), bombesin, factor IX, thrombin, hemopoietic growth factor, tumor necrosis factor-alpha and -beta, enkephalinase, human serum albumin, mullerian-inhibiting substance, mouse gonadotropin-associated peptide, a microbial protein, beta-lactamase, tissue factor protein, inhibin, activin, vascular endothelial growth factor, receptors for hormones or growth factors; integrin, thrombopoietin, protein A or D, rheumatoid factors, nerve growth factors, NGF-β, platelet-growth factor, transforming growth factors (TGF), TGF-alpha, TGF-beta, insulin-like growth factor-I or -II, insulin-like growth factor binding proteins, DNase, latency associated peptide, erythropoietin, osteoinductive factors, interferons, interferon-alpha, interferon-beta, interferon-gamma, colony stimulating factors (CSFs), M-CSF, GF-CSF, and G-CSF, interleukins (ILs), IL-1, IL-2, IL-3, IL-4, superoxide dismutase; decay accelerating factor, viral antigens, HIV envelope proteins, GP120, GP140, and atrial natriuretic peptides A, B or C;

22. The method according to item 21, wherein said POI is an antibody, antibody fragment, single chain antibody, scFv, scFab, or single domain antibody;

23. A helper phage such as VCSM13 or M13K07 with a modification of the phage DNA to express a capture sequence-anchor sequence fusion protein or a tether sequence-anchor sequence fusion protein which can be used to infect prokaryotic cells to produce phage which carry capture or tether sequence on its surface;

24. The phage according to item 23, wherein said tethering sequence is selected from a SpyTag sequence selected from any one of SEQ ID NOs: 1, 3, 5, 6, 25 or 27 a protein with at least 70% sequence identity to an amino acid sequence as set forth in any one of SEQ ID NOs: 1, 3, 5, 6, 25 or 27, a SnoopTag sequence selected from any one of SEQ ID NOs: 13, 7, 11, 9, 10 or 15 or a protein with at least 70% sequence identity to an amino acid sequence as set forth in any one of SEQ ID NOs: 13, 7, 11, 9, 10 or 15, a sortase recognition domain or a sortase bridging domain, a butelase recognition motif or a split intein;

25. The phage according to item 23, wherein capture sequence is a SpyCatcher sequence selected from any one of SEQ ID NOs: 1, 3, 5, 6, 26 or 28 a protein with at least 70% sequence identity to an amino acid sequence as set forth in any one of SEQ ID NOs: 1, 3, 5, 6, 26 or 28, a SnoopCatcher sequence selected from any one of SEQ ID NOs: 13, 7, 11, 9, 10 or 15 or a protein with at least 70% sequence identity to an amino acid sequence as set forth in any one of SEQ ID NOs: 13, 7, 11, 9, 10 or 15, a sortase recognition domain or a sortase bridging domain, a butelase recognition motif or a split intein;

26. A prokaryotic or eukaryotic host cell with a modified genome to express a capture sequence-anchor sequence fusion protein or a tether sequence-anchor sequence fusion protein which can be used to display capture or tether sequence on its surface or on the surface of a virus or phage produced by the host cell; and/or a modified genome to express a ligase derived from SEQ ID NOs: 13, 7, 11, 9, 10 or 15 or a ligase having at least 70% sequence identity to a ligase derived from SEQ ID NOs: 13, 7, 11, 9, 10 or 15; a vector comprising a promoter operably linked to a comprising a polynucleotide encoding a sortase; or a vector comprising a promoter operably linked to a polynucleotide encoding a butelase;

27. The prokaryotic or eukaryotic host cell according to item 26, wherein said tethering sequence is selected from a SpyTag sequence selected from any one of SEQ ID NOs: 1, 3, 5, 6, 25 or 27 a protein with at least 70% sequence identity to an amino acid sequence as set forth in any one of SEQ ID NOs: 1, 3, 5, 6, 25 or 27, a SnoopTag sequence selected from any one of SEQ ID NOs: 13, 7, 11, 9, 10 or 15 or a protein with at least 70% sequence identity to an amino acid sequence as set forth in any one of SEQ ID NOs: 13, 7, 11, 9, 10 or 15, a sortase recognition domain or a sortase bridging domain, a butelase recognition motif or a split intein; and 28. The prokaryotic or eukaryotic host cell according to item 26, wherein capture sequence is a SpyCatcher sequence selected from any one of SEQ ID NOs: 1, 3, 5, 6, 26 or 28 a protein with at least 70% sequence identity to an amino acid sequence as set forth in any one of SEQ ID NOs: 1, 3, 5, 6, 26 or 28, a SnoopCatcher sequence selected from any one of SEQ ID NOs: 13, 7, 11, 9, 10 or 15 or a protein with at least 70% sequence identity to an amino acid sequence as set forth in any one of SEQ ID NOs: 13, 7, 11, 9, 10 or 15, a sortase recognition domain or a sortase bridging domain, a butelase recognition motif or a split intein.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting.

Example 1

Covalent Capture Display

This example describes the covalent display of human Fab fragments, adalimumab and trastuzumab, with a SpyTag at the C-terminus of the heavy chain on the surface of M13 phages which have a SpyCatcher fused to the N-terminus of the pIII. SpyTag and SpyCatcher form a covalent bond within the *E. coli* that leads to a covalent linkage of the Fab to the pIII phage coat protein.

Modification of Helperphages to Produce SpyCatcher-pIII

Figure 2:
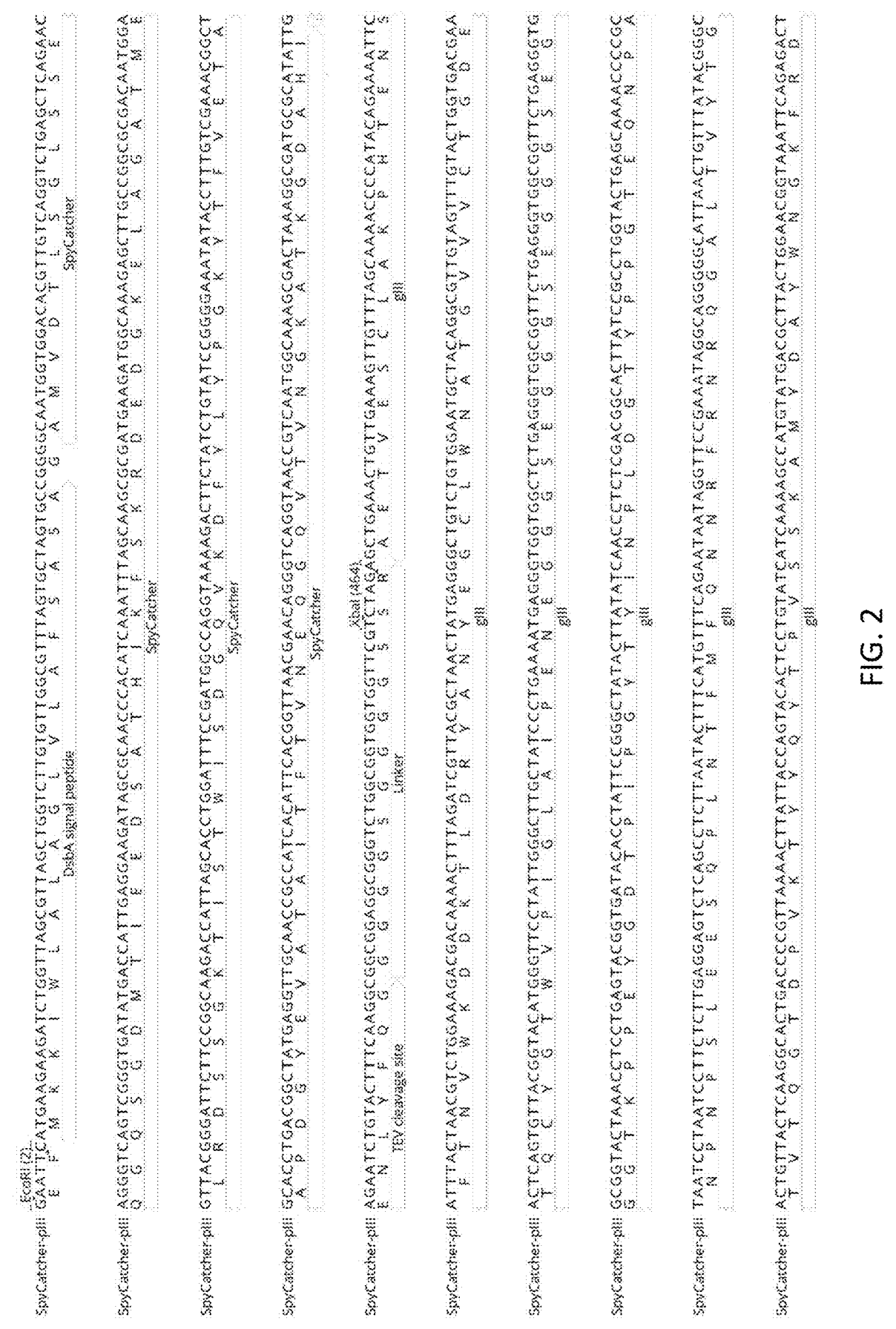
Figure 2:
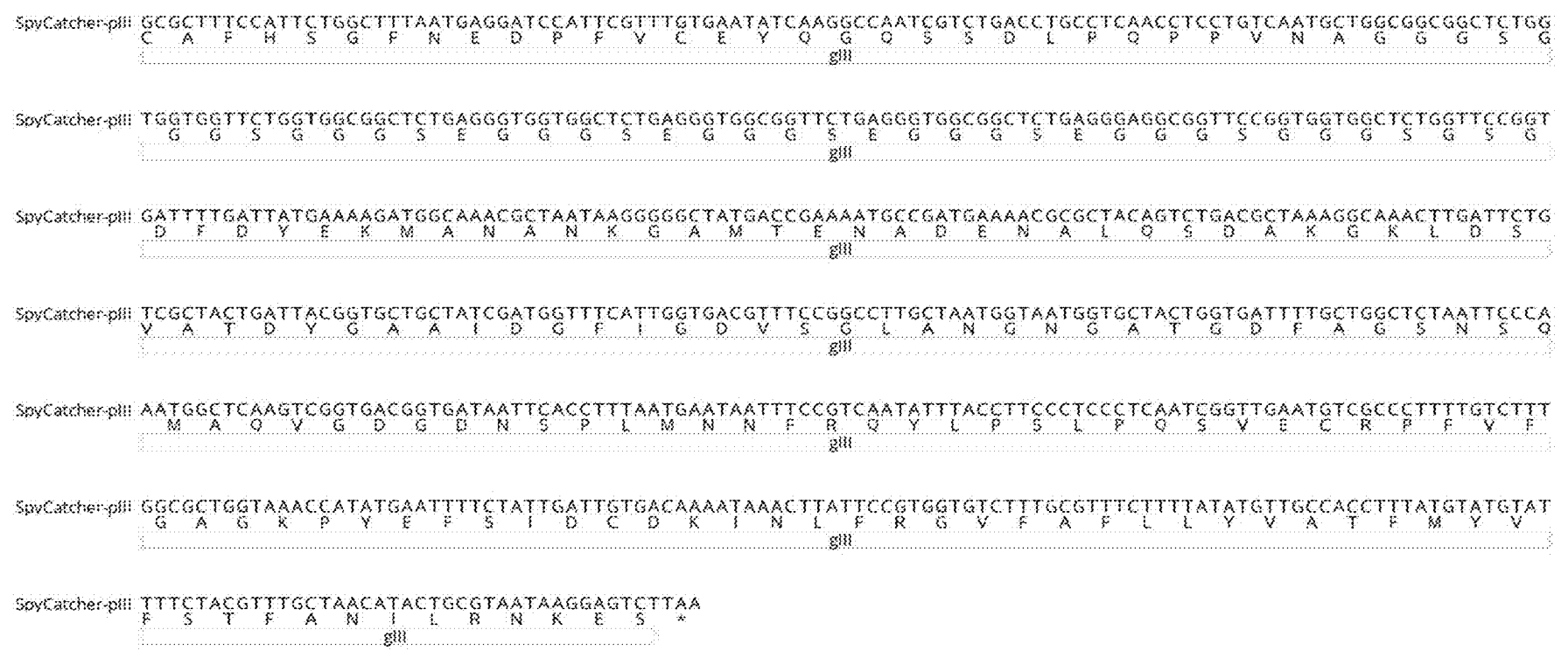

VCSM13 helperphage were modified to replace the gIII with a SpyCatcher-gIII genetic fusion. Cloning was done by ligation of restriction digested PCR products. The phage genome was PCR amplified and restriction sites were inserted with primers at the beginning of the gIII (forward primer with XbaI site) and before the start codon of the gIII (reverse primer with EcoRI site) omitting the gIII signal peptide. The inserted sequence with matching restriction sites consists of a DsbA signal peptide, SpyCatcher, TEV protease cleavage site and a short linker (GGGGSGGGGS, SEQ ID NO: 33, FIG. 2). After transformation into *E. coli* XL1 Blue F' competent cells, clones with correct insert were identified by colony PCR to distinguish the shorter wt gIII from the SpyCatcher-gIII Correct insertion was confirmed by sequencing the relevant region of PCR amplified phage DNA.

Production of SpyCatcher-pIII Helperphage

XL1F' carrying the modified helperphage genome were grown in 50 ml 2×YT with kanamycin at 37° C. overnight. Next day, six 300 ml cultures were inoculated from the overnight culture to OD600 of 0.1 and grown in 2×YT with kanamycin at 37° C. to an OD600 of ~0.6 and then transferred to 18° C. for helperphage production overnight. Bacteria were spun down and phage were purified and concentrated from the supernatant by PEG precipitation as described below. The phage pellet was dissolved in 1000 µl PBS and after addition of 20% glycerol aliquots were stored at −80° C.

XL1 Blue F', MC1061 F' or TG1F' cells were grown in 2×YT to an OD600 of 0.6-0.8 and then infected with the modified helperphage for 45 min without shaking and 45 min with shaking. The culture was incubated on a shaker at 37° C. for 3-4 h and was then transferred to a larger volume of 2×YT with 50 µg/ml kanamycin (e.g. 50 ml culture and 350 ml 2×YT) for overnight phage production at 18° C. The next day, the phages were precipitated as described below, dissolved in 400 µl PBS and stored at −80° C. after addition of 20% glycerol.

Phage PEG Precipitation

Phage were precipitated from the overnight culture supernatant by addition of ¼ the volume +10% of ice cold PEG/NaCl solution (20% PEG 6000, 2.5M NaCl). Supernatant was incubated on ice on a shaker for 30 min and phages were centrifuged at 13,000×g for 60 min at 2-8° C. The supernatant was discarded and the pellet resuspended in 10 ml PBS. Remaining bacteria were removed from the phage solution by sterile filtration with a 0.22 µm filter and PEG/NaCl precipitation was repeated as described. The phage pellet was dissolved in PBS.

SpyCatcher-pIII Helperphage Analysis

1. Spot Titration

Phage titer and infectivity were determined by spot titration and by ELISA. For spot titration, a culture was inoculated with a TG1F' colony from a M9 minimal agar plate and grown to OD600 of 0.6-0.8 at 37° C. A 1:10 dilution series of the helperphage in 2×YT was prepared and 10 µl of the dilution was mixed with 90 µl TG1F' culture, incubated at 37° C. for 30 min and then 5 µl were plated on a LB agar plate containing 1% glucose and 50 µg/ml kanamycin and incubated at 37° C. overnight. Unmodified VCSM13 helperphages were used as a reference. Colonies in spots with less than 30 colonies were counted and the titer was calculated according to the dilution and used volumes. Titers were ~$10^{11}$ cfu/ml.

2. ELISA

Determination of the phage titer and proof of display of the SpyCatcher on the phage surface was done by ELISA. An ELISA microtiter plate was coated at 4° C. overnight with an anti-M13 antibody (anti-pVIII, 1 µl/ml in PBS) and anti-SpyCatcher Fab (5 µg/ml in PBS), respectively. After blocking with Chemiblocker in TBST at room temperature for 1-2 h, a 1:2 dilution series of modified helperphage and wt VCSM13 helperphage with known titer were added to the ELISA plate and incubated at room temperature for 1 h.

Detection was performed with an anti-M13 HRP detection antibody and QuantaBlu peroxidase fluorescence substrate. The titer estimated by this method was at ~$5\times10^{13}$ phage/ml. The ELISA with anti-SpyCatcher capture antibody gave a strong signal thus confirming the presence of phage with one or more SpyCatchers displayed on the surface.

3. Western Blot

Presence of the SpyCatcher on the surface of the phage was also confirmed by Western blot of denatured phage with an anti-SpyCatcher antibody and an anti-pIII antibody, respectively. A Bio-Rad Mini-PROTEAN™ Vertical Electrophoresis Cell was used along with a Mini-Protean TGX 4-20% gel and the Bio-Rad Precision Plus Protein Standard molecular weight marker. Proteins were blotted to a PVDF membrane by using the Bio-Rad Trans-Blot Turbo Transfer System. The membrane was blocked with milk in TBST for 1 h on a shaker followed by incubation for 1 h with either one of the two primary antibodies. Secondary antibody for the anti-SpyCatcher primary was an HRP conjugated anti-hFab antibody, for anti-pIII an HRP conjugated anti-mouse IgG antibody was used. Clarity Western ECL substrate was used for detection.

Figures 3A, 3B:
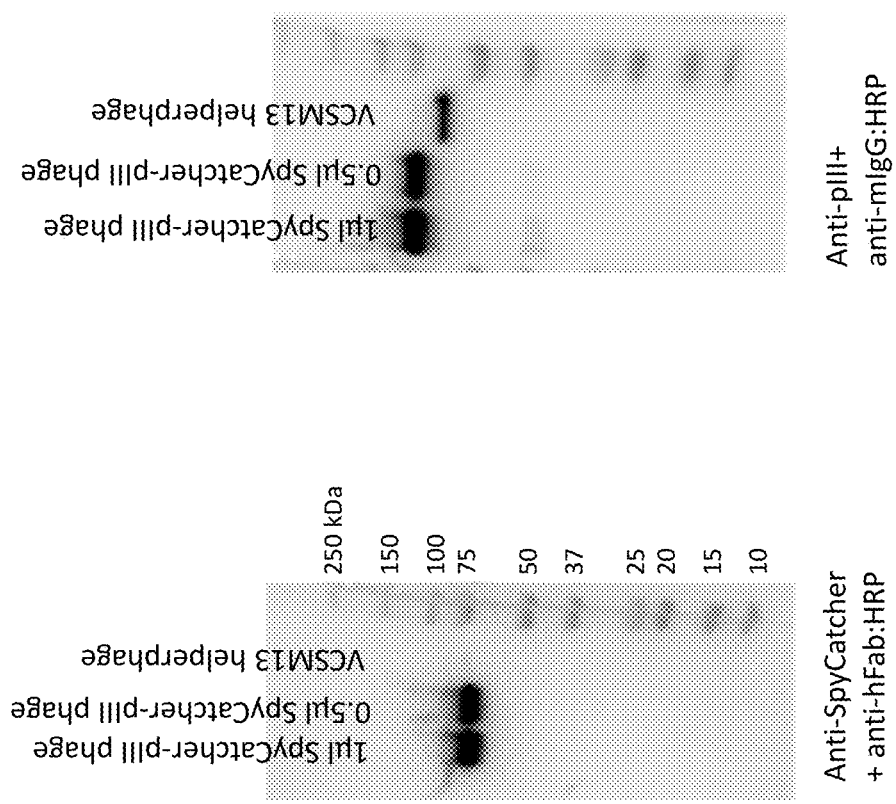
FIGS. 3A-3B illustrate Western blot analysis of SpyCatcher phage compared to VCSM13 phage.

The Western blot with anti-SpyCatcher detection shows a band for SpyCatcher phages only but not for VCSM13 phages (negative control; FIG. 3A). The blot with anti-pIII detection shows that the pIII band in SpyCatcher phages runs higher than VCSM13 phages. The shift equaled the increase in molecular weight by the SpyCatcher fused to the pIII (FIG. 3B).

Fab-SpyTag constructs

Human Fab antibody fragments (trastuzumab and adalimumab) with a SpyTag (Spy) and hexahistidine tag (H) at the C-terminus of the heavy chain were cloned into a bicistronic expression vector pBBx1, consisting of a lac promoter, Shine-Dalgarno (SD) sequence, start codon, pelB leader sequence, Fab light chain stop codon, SD sequence, start codon, ompA leader sequence Fab heavy chain, SpyTag, His tag, and stop codon. The vector furthermore carries a ColE1 and f1 origin of replication, a chloramphenicol resistance and lac repressor (LacI).

Covalent Capture Display

The plasmids described above were transformed into TG1F' cells. A freshly inoculated culture was grown overnight in 5 ml 2×YT with chloramphenicol and 1% glucose at 37° C. on a shaker. Next day, a 100 ml culture was inoculated with this preculture to an OD600 of 0.05 and grown at 37° C. to an OD600 of 0.5. 50 ml of this culture were infected with SpyCatcher-pIII helperphages at 37° C. for 45 min without shaking and 45 min with shaking. Bacteria were spun down and the supernatant was discarded. The pellet was resuspended in 300 ml 2×YT with chloramphenicol, kanamycin, and 0.25 mM IPTG and cultured overnight at 30° C. for phage production. Bacteria were spun down and phages were PEG precipitated from the supernatant as described before. The phage pellet was dissolved in 500-1000 µl PBS and stored at −80° C. after addition of 20% glycerol.

Analysis of Covalent Capture Display Fab Phages

1. Spot Titration

Spot titration was performed as described for the SpyCatcher-pIII phages. Titers were in the range of $1-3\times10^{13}$ cfu.

2. ELISA

Phage ELISA was performed as described above for the SpyCatcher-pIII phages. Fab displaying phages with known titer were used as a standard to determine the phage titer. Titers determined with this method were in the range of $1 \times 10^{14}$ phages/ml.

Instead of the anti-SpyCatcher antibody an anti-Fd capture antibody was used for the second ELISA. This antibody can capture phages which carry a Fab heavy chain (Fd) on the surface of the phages and thus this assay confirms a successful Fab covalent capture display. This ELISA gave a strong signal thus indicating a good display rate of most likely several Fab per phage.

3. Western Blot

Figure 4:
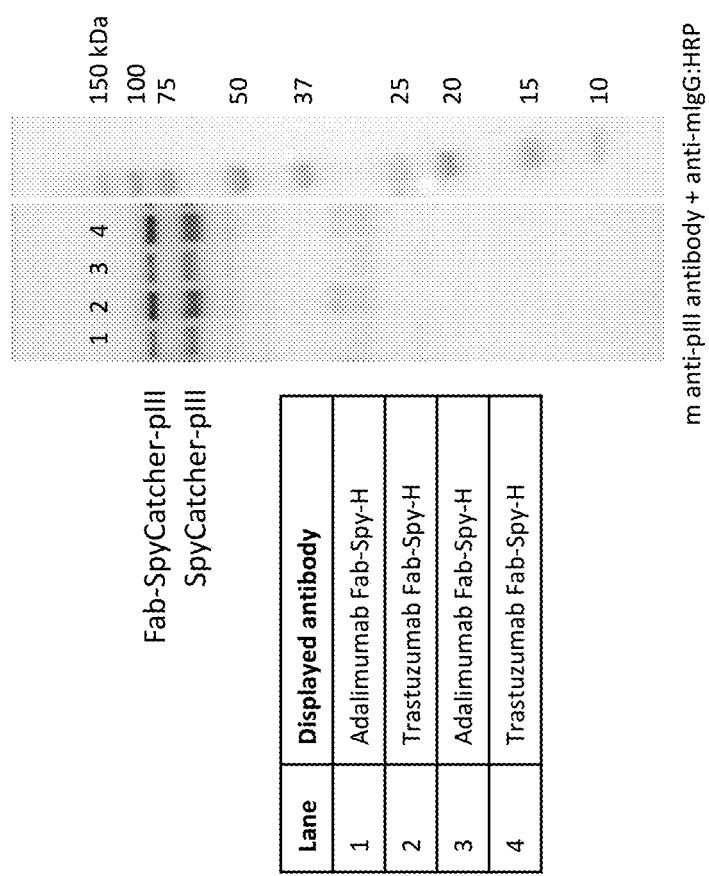
FIG. 4 is a Western blot of Fab phages. The Fab expressing phages were analyzed by Western blot with an anti-pIII antibody. Two main bands are visible, the Fab-SpyTag- SpyCatcher-pIII and SpyCatcher-pIII fusion protein (FIGS. 3A-3B). The intensity ratio of the two bands indicates an average display rate of approximately 2 Fab per phage (each phage carries ~5 pIII proteins at the tip of the coat).

Fab phages were analyzed by Western blot with an anti-pIII antibody. Western blot was performed as described above for SpyCatcher-pIII phages. Two main bands are visible, the Fab-SpyTag-SpyCatcher-pIII and SpyCatcher-pIII fusion protein (FIG. 4). The intensity ratio of the two bands indicates an average display rate of approximately 2 Fab per phage (each phage carries ~5 pIII proteins at the tip of the coat).

4. Functionality—Antigen Binding

Figure 5:
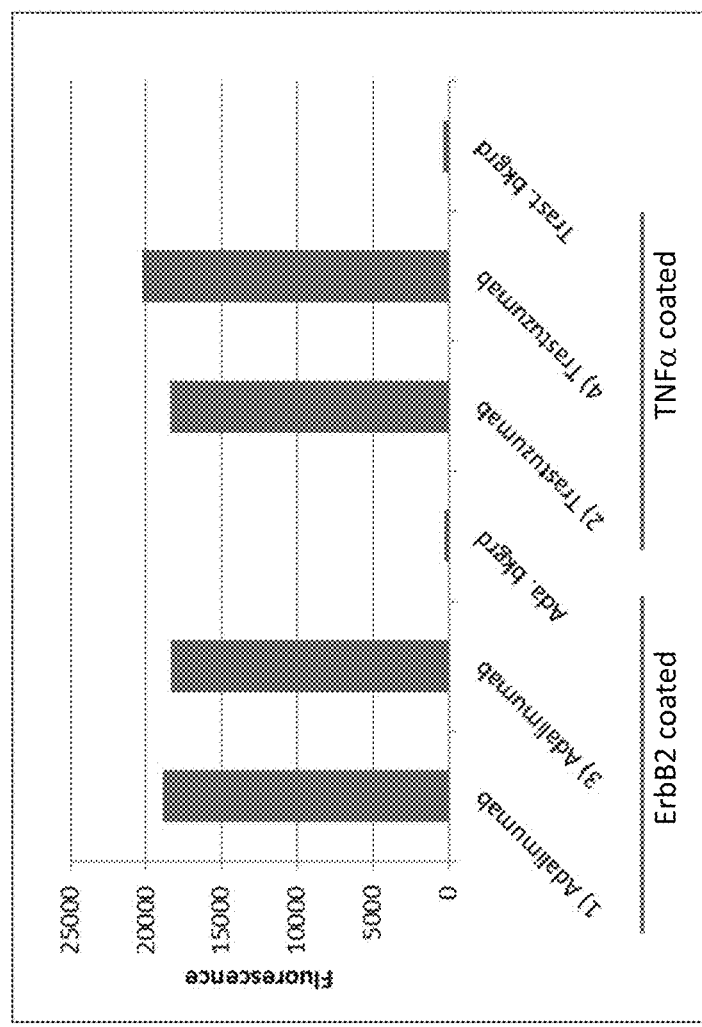
FIG. 5 demonstrates proper folding of the Fab on the surface of the phage. Fab displaying phages were analyzed by ELISA for antigen binding capability (TNFα for Adalimumab and ErbB2 for Trastuzumab). Both Fab phages demonstrated a strong signal over background value which confirms the functionality of the Fab on the surface of the phage.

To confirm proper folding of the Fab on the surface of the phage, Fab displaying phages were also analyzed by ELISA for antigen binding capability. Fab antigens, TNF-α for Adalimumab and ErbB2 for Trastuzumab, were coated on an ELISA plate at 5 µg/ml in PBS overnight at 4° C. After blocking with Chemiblocker in TBST for 1 h, the plate was incubated with a 1:500 dilution of the Fab phage in TBST for 1 h. Phages were detected with an HRP-conjugated anti-M13 antibody and QuantaBlu fluorescence substrate. For both Fab phages a strong signal over background value confirmed functionality of the Fab on the surface of the phage (FIG. 5).

5. Phagemid DNA Retrieval After Phage Infection

To confirm that the Fab-displaying phages carry the phagemid TG1F' was infected with the Fab phages and DNA of single colonies was analyzed for phagemid by PCR.

1 ml of a culture of TG1F' in 2×YT at OD600 of 0.4-0.6 was infected with 10 µl Fab phages and incubated at 37° C. without shaking for 45 min followed by 45 min with shaking. Different amounts of this culture (10 µl, 1 µl, and 0.1 µl) were plated on LB agar plates with chloramphenicol and glucose. Single colonies were picked for a colony-PCR with primers which anneal in the pBBx1 phagemid. The presence of a PCR product of correct size was confirmed for all colonies by agarose gel electrophoresis.

REFERENCES

Bastien, N., Trudel, M., and Simard, C., 1997, Protective immune responses induced by the immunization of mice with a recombinant bacteriophage displaying an epitope of the human respiratory syncytial virus. Virology 234:118-122.

Batonick, M., Kiss, M. M., Fuller, E. P., Magadan, C. M., Holland, E. G., Zhao, Q., Wang, D., Kay, B. K., Weiner, M. P., 2016, pMINERVA: A donor-acceptor system for the in vivo recombineering of scFv into IgG molecules. J Immunol Methods 431:22-30.

Benhar, I., 2001, Biotechnological applications of phage and cell display. Biotechnol Adv 19:1-33.

Borodina, I., Jensen, B. M., Søndergaard, I., and Poulsen, L. K., 2010, Display of wasp venom allergens on the cell surface of Saccharomyces cerevisiae. Microb Cell Fact 9:74.

Caspi, J. et al., 2003, Distribution of split DnaE inteins in cyanobacteria. Mol Microbiol. 50: 1569-1577.

Chang and Lo, 2000, Modification with a phosphorylation tag of PKA in the TraT-based display vector of Escherichia coli. J Biotechnol 78:115-122.

Chen, W. and Georgiou, G., 2002, Cell-surface display of heterologous proteins: From high-throughput screening to environmental applications. Biotechnol Bioeng 79:496-503.

Chesnut, J. D. et al., 1996, Selective isolation of transiently transfected cells from a mammalian cell population with vectors expressing a membrane anchored single-chain antibody. J Immunological Methods. 193(1):17-27.

Choi, J. et al., 2006, Protein Trans-splicing and Characterization of a Split Family B-type DNA Polymerase from the Hyperthermophilic Archaeal Parasite Nanoarchaeum equitans. J Mol Biol. 356: 1093-1106.

Dassa, B. et al., 2007, Trans Protein Splicing of Cyanobacterial Split Inteins in Endogenous and Exogenous Combinations. Biochemistry. 46:322-330.

Duc, L. H., Hong, H. A., Atkins, H. S., Flick-Smith, H. C., Durrani, Z., Rijpkema, S., et al., 2007, Immunization against anthrax using Bacillus subtilis spores expressing the anthrax protective antigen. Vaccine 25:346-355.

Fierer, J. O., Veggiani, G., Howarth, M., 2014, SpyLigase peptide-peptide ligation polymerizes affibodies to enhance magnetic cancer cell capture. Proc Natl Acad Sci USA. 111: E1176-1181.

Gao, C. S., Mao, S. L., Lo, C. H. L., Wirsching, P., Lerner, R. A., Janda, K. D., 1999, Making artificial antibodies: A format for phage display of combinatorial heterodimeric arrays. PNAS 96(11):6025-30.

Georgiou, G. et al., 1996, Display of β-lactamase on the Escherichia coli surface: outer membrane phenotypes conferred by Lpp'-OmpA'-β-lactamase fusions. Protein Eng 9: 239-247.

Gleiter, S., and Lilie, H., 2001, Coupling of antibodies via protein Z on modified polyoma virus-like particles. Protein Sci 10:434-444.

Ho, M. et al, 2006, Isolation of anti-CD22 Fv with high affinity by Fv display on human cells. PNAS, 103:9637-9642.

Ilk, N., Schumi, C. T., Bohle, B., Egelseer, E. M., and Sleytr, U. B., 2011, Expression of an endotoxin-free S-layer/allergen fusion protein in gram-positive Bacillus subtilis 1012 for the potential application as vaccines for immunotherapy of atopic allergy. Microb Cell Fact 10:6.

Isticato, R., Cangiano, G., Tran, H. T., Ciabattini, A., Medaglini, D., Oggioni, M. R. et al., 2001, Surface display of recombinant proteins on Bacillus subtilis spores. J Bacteriol 183:6294-6301.

Jung, H. C. et al., 1998, Surface display of Zymomonas mobilis levansucrase by using the ice-nucleation protein of Pseudomonas syringae. Nat Biotechnol 16:576-580.

Keeble, A. H., Banerjee, A., Ferla, M. P., Reddington, S. C., Khairil Anuar, I. N. A., Howarth, M., 2017, Evolving accelerated amidation by SpyTag/SpyCatcher to analyze membrane dynamics. Ange, Chem. Int. Ed. 56:16521-16525.

Koutsky, L. A., Ault, K. A., Wheeler, C. M., Brown, D. R., Barr, E., Alvarez, F. B. et al., 2002, A controlled trial of a human papillomavirus type 16 vaccine. N Engl J Med 347:1645-1651.

Lee, S. H. et al., 2004, Display of Bacterial Lipase on the Escherichia coli Cell Surface by Using FadL as an Anchoring Motif and Use of the Enzyme in Enantioselective Biocatalysis. Appl Environ Microbiol 70:5074-5080.

Li, L., Kang, D. G., and Cha, H. J., 2003, Functional display of foreign protein on surface of *Escherichia coli* using N-terminal domain of ice nucleation protein. Biotechnol Bioeng 85:214-221.

Little, M. et al., 1994, Surface display of antibodies, Biotechnol Adv. 12(3):539-555.

Liu, X. and Yang J., 2003, Split dnaE Genes Encoding Multiple Novel Inteins in *Trichodesmium erythraeum*. J Biol Chem. 278:26315-26318.

Lu, Z., Murray, K. S., Cleave, V. V., LaVallie, E. R., Stahl, M. L., and McCoy, J. M., 1995, Expression of thioredoxin random peptide libraries on the *Escherichia coli* surface as functional fusions to flagellin: a system designed for exploring protein-protein interactions. Bio/Technology 13:366-372.

Matsumoto, T., Fukuda, H., Ueda, M., Tanaka, A., and Kondo, A., 2002, Construction of yeast strains with high cell surface lipase activity by using novel display systems based on the Flo1p flocculation functional domain. Appl Environ Microbiol 68:4517-4522.

Mauriello, E. M., Duc, L. H., Isticato, R., Cangiano, G., Hong, H. A., De, F. M. et al., 2004, Display of heterologous antigens on the *Bacillus subtilis* spore coat using CotC as a fusion partner. Vaccine 22:1177-1187.

Mazor, Y., Van Blarcom, T., Carroll, S., Georgiou, G., 2010, Selection of full-length IgGs by tandem display on filamentous phage particles *Escherichia coli* fluorescence-activated cell sorting screening. The FEBS Journal. 277 (10):2291-2303.

McCafferty, J., Griffiths, A. D., Winter, G., and Chiswell, D. J., 1990, Phage antibodies: filamentous phage displaying antibody variable domains. Nature 348:552-554.

Nguyen, G. K. T., Wang, S., Qiu, Y., Hemu, X., Lian, Y., Tam, J. P., 2014, Butelase 1 is an Asx-specific ligase enabling peptide macrocyclization and synthesis. Nat Chem Biol. 10:732-738.

Nomellini, J. F., Duncan, G., Dorocicz, I. R., and Smit, J., 2007, S-layer-mediated display of the immunoglobulin G-binding domain of streptococcal protein G on the surface of *Caulobacter crescentus*: development of an immunoactive reagent. Appl Environ Microbiol 73:3245-3253.

Qi, H., Lu, H., Qiu, H. J., Petrenko, V., Liu, A., 2012, Phagemid vectors for phage display:
properties, characteristics and construction. J Mol Biol. 417(3):129-143.

Reddington, S. C., Howarth, M., 2015, Secrets of a covalent interaction for biomaterials and biotechnology: SpyTag and SpyCatcher. Current opinion in chemical biology. 29:94-99.

Rondot, S., Koch, J., Breitling, F., Dubel, S., 2001, A helper phage to improve single-chain antibody presentation in phage display. Nat Biotechnol. 19(1):75-78.

Rothe, C., Urlinger, S., Lohning, C., Prassler, J., Stark, Y., Jager, U. et al., 2008, The human combinatorial antibody library HuCAL GOLD combines diversification of all six CDRs according to the natural immune system with a novel display method for efficient selection of high-affinity antibodies. J Mol Biol. 376(4):1182-1200.

Samuelson, P., Gunneriusson, E., Nygren, P. A., and Stahl, S., 2002, Display of proteins on bacteria. J Biotechnol 96:129-154.

Schmohl, L., Schwarzer, D., 2014, Sortase-mediated ligations for the site-specific modification of proteins. Current Opinion in Chemical Biology. 22:122-128.

Shao, X., Jiang, M., Yu, Z., Cai, H., and Li, L., 2009, Surface display of heterologous proteins in *Bacillus thuringiensis* using a peptidoglycan hydrolase anchor. Microb Cell Fact 8:48.

Shimojo, R., Furukawa, H., Fukuda, H., and Kondo, A., 2004, Preparation of yeast strains displaying IgG binding domain ZZ and EGFP for novel antigen detection system. J Biosci Bioeng 96:493-495.

Steidler, L., Viaene, J., Fiers, W., and Remaut, E., 1998, Functional display of a heterologous protein on the surface of *Lactococcus lactis* by means of the cell wall anchor of *Stpaphylococcus aureus* protein A. Appl Environ Microbiol 64:342-345.

Strauss, A. and Gotz. F., 1996, In vivo immobilization of enzymatically active polypeptides on the cell surface of *Staphylococcus carnosus*. Mol Microbiol 21:491-500.

Tesar, D., Hötzel, I., 2013, A dual host vector for Fab phage display and expression of native IgG in mammalian cells. Protein Eng Des Sel 26:655-662.

Thiel, I. V., Volkmann, G., Pietrokovski, S., Mootz, H. D., 2014, An atypically split intein engineered for a highly efficient protein labeling. Angew Chem Int Ed Engl. 53:1306-1310.

Toplak, A., Nuljens, T., Quaedflieg, P. J. L., Wu, B., Janssen, D. B., 2016, Peptiligase, an enzyme foe efficient chemoenzymatic peptide synthesis and cyclization in water. Adv Synth Catal. 358:32140-32147.

Tornetta, M., Reddy, R., Wheeler, J. C., 2012, Selection and maturation of antibodies by phage display through fusion to pIX. Methods 58(1):34-9.

Veggiani, G. et al., 2016, Programmable polyproteams built using twin peptide superglues. Proc Natl Acad Sci USA 113:1202-1207.

Veiga, E. et al., 2003, Autotransporters as Scaffolds for Novel Bacterial Adhesins: Surface Properties of *Escherichia coli* Cells Displaying Jun/Fos Dimerization Domains. J Bacteriol 185:5585-5590.

Wang, K. C., Wang, X., Zhong, P., Luo, P. P., 2010, Adapter-directed display: a modular design for shuttling display on phage surfaces. J Mol Biol. 395:1088-1101.

Ward, R. L., Clark, M. A., Lees, J., Hawkins, N. J., 1996, Retrieval of human antibodies from phage-display libraries using enzymatic cleavage. J Immunol Methods. 189 (1):73-82.

Wen, F., Sun, J., and Zhao, H., 2010, Yeast surface display of trifunctional minicellulosomes for simultaneous sac-charifi-cation and fermentation of cellulose to ethanol. Appl Environ Microbiol 76:1251-1260.

Westerlund-Wikstrom, B. et al., 1997, Functional expression of adhesive peptides as fusions to *Escherichia coli* flagellin. Protein Eng 10:1319-1326.

Wieczorek, A. S., and Martin, V. J. J. (2010) Engineering the cell surface display of cohesins for assembly of cellulosome-inspired enzyme complexes on *Lactococcus lactis*. Microb Cell Fact 9:69.

Wu, H. et al., 1998, Protein trans-splicing by a split intein encoded in a split DnaE gene of *Synechocystis* sp. PCC6803. Proc Natl Acad Sci USA. 95:9226-9231.

Zakeri, B. et al., 2012, Peptide tag forming a rapid covalent bond to a protein, through engineering a bacterial adhesion. Proc Natl Acad Sci USA. 109: E690-697.

Zettler, J. et al., 2009, The Naturally Split Npu DnaE Intein Exhibits an Extraordinarily High Rate in the Protein Trans-Splicing Reaction. FEBS Letters. 553:909-914.

I claim:

1. A combination of vectors comprising:
   a) a first vector comprising a genetic construct (GC1) comprising polynucleotide encoding a protein of interest (POI) fused, in frame, to a tether sequence; and
   b) a second vector comprising a genetic construct (GC2) comprising polynucleotide encoding an anchor protein fused, in frame, to a capture sequence, the tether sequence and capture sequence forming a covalent bond when brought into contact with one another either spontaneously or with the help of an enzyme; or a combination of vectors comprising:
   a) a first vector comprising a genetic construct (GC1) comprising polynucleotide encoding a protein of interest (POI) fused, in frame, to a capture sequence; and
   b) a second vector comprising a genetic construct (GC2) comprising polynucleotide encoding an anchor protein fused, in frame, to a tether sequence, the tether sequence and capture sequence forming a covalent bond when brought into contact with one another either spontaneously or with the help of an enzyme, wherein:
   said anchor protein is selected from alpha-agglutinin 1, alpha-agglutinin 2, Cwp1, Cwp2, Gas1p, Yap3p, Flo1p, Crh2p, Pir1, Pir2, Pir4, Icwp, HpSEDI, HpGASI, HpTIPI, HPWPI, HwpIp, Als3p, or Rbt5;
   said tether sequence comprises SEQ ID NO: 27, a sequence having at least 70% sequence identity to SEQ ID NO: 27, SEQ ID NO: 34, or SEQ ID NO: 48;
   said capture sequence comprises SEQ ID NO: 28, a sequence having at least 90% sequence identity to SEQ ID NO: 28, or amino acids 22-137 of SEQ ID NO: 30; and
   said POI is selected from antibodies, antibody fragments, single chain antibodies, scFv, scFab, or single domain antibodies.

2. The combination of vectors according to claim 1, wherein each vector comprises transcriptional or translational control sequences for expressing the POI and anchor protein.

3. The combination of vectors according to claim 2, wherein said transcription or translational control sequences are selected from replication origins, promoters, enhancers, repressor binding regions, transcription initiation sites, ribosome binding sites, translation initiation sites, and termination sites for transcription and translation.

4. A yeast host cell comprising a combination of vectors according to claim 1.

5. The combination of vectors according to claim 1, wherein:
   said anchor protein is alpha-agglutinin 1;
   said tether sequence comprises SEQ ID NO: 27; and
   said capture sequence comprises SEQ ID NO: 28.

6. The combination of vectors according to claim 1, wherein:
   said anchor protein is alpha-agglutinin 1;
   said tether sequence comprises a sequence having at least 70% sequence identity to SEQ ID NO: 27; and
   said capture sequence comprises SEQ ID NO: 28.

7. The combination of vectors according to claim 1, wherein:
   said anchor protein is alpha-agglutinin 1;
   said tether sequence comprises SEQ ID NO: 48; and
   said capture sequence comprises SEQ ID NO: 28.

8. The combination of vectors according to claim 1, wherein:
   said anchor protein is alpha-agglutinin 1;
   said tether sequence comprises SEQ ID NO: 34; and
   said capture sequence comprises SEQ ID NO: 28.

9. The combination of vectors according to claim 1, wherein:
   said anchor protein is alpha-agglutinin 1;
   said tether sequence comprises SEQ ID NO: 27; and
   said capture sequence comprises a sequence having at least 90% sequence identity to SEQ ID NO: 28.

10. The combination of vectors according to claim 1, wherein:
    said anchor protein is alpha-agglutinin 1;
    said tether sequence comprises a sequence having at least 70% sequence identity to SEQ ID NO: 27; and
    said capture sequence comprises a sequence having at least 90% sequence identity to SEQ ID NO: 28.

11. The combination of vectors according to claim 1, wherein:
    said anchor protein is alpha-agglutinin 1;
    said tether sequence comprises SEQ ID NO: 48; and
    said capture sequence comprises a sequence having at least 90% sequence identity to SEQ ID NO: 28.

12. The combination of vectors according to claim 1, wherein:
    said anchor protein is alpha-agglutinin 1;
    said tether sequence comprises SEQ ID NO: 34; and
    said capture sequence comprises a sequence having at least 90% sequence identity to SEQ ID NO: 28.

13. The combination of vectors according to claim 1, wherein:
    said anchor protein is alpha-agglutinin 1;
    said tether sequence comprises SEQ ID NO: 27; and
    said capture sequence comprises amino acids 22-137 of SEQ ID NO: 30.

14. The combination of vectors according to claim 1, wherein:
    said anchor protein is alpha-agglutinin 1;
    said tether sequence comprises a sequence having at least 70% sequence identity to SEQ ID NO: 27; and
    said capture sequence comprises amino acids 22-137 of SEQ ID NO: 30.

15. The combination of vectors according to claim 1, wherein:
 said anchor protein is alpha-agglutinin 1;
 said tether sequence comprises SEQ ID NO: 34; and
 said capture sequence comprises amino acids 22-137 of SEQ ID NO: 30.

16. The combination of vectors according to claim 1, wherein:
 said anchor protein is alpha-agglutinin 1;
 said tether sequence comprises SEQ ID NO: 48; and
 said capture sequence comprises amino acids 22-137 of SEQ ID NO: 30.

\* \* \* \* \*